(12) United States Patent
Suh et al.

(10) Patent No.: US 9,506,118 B2
(45) Date of Patent: Nov. 29, 2016

(54) FIBROBLAST GROWTH FACTOR-2 (FGF2) AND SYNDECAN-1 (SDC1) AS BIOMARKERS FOR POOR OUTCOME HODGKIN LYMPHOMA PATIENTS

(71) Applicants: K. Stephen Suh, Hackensack, NJ (US); Andre Goy, New York, NY (US)

(72) Inventors: K. Stephen Suh, Hackensack, NJ (US); Andre Goy, New York, NY (US)

(73) Assignee: Hackensake University Medical Center, Hackensack, NJ (US)

( * ) Notice: Subject to any disclaimer, the term of this patent is extended or adjusted under 35 U.S.C. 154(b) by 0 days.

(21) Appl. No.: 14/640,824

(22) Filed: Mar. 6, 2015

(65) Prior Publication Data
US 2015/0252433 A1 Sep. 10, 2015

Related U.S. Application Data

(60) Provisional application No. 61/949,629, filed on Mar. 7, 2014.

(51) Int. Cl.
*C12Q 1/68* (2006.01)

(52) U.S. Cl.
CPC ........ *C12Q 1/6886* (2013.01); *C12Q 2600/106* (2013.01); *C12Q 2600/158* (2013.01)

(58) Field of Classification Search
None
See application file for complete search history.

(56) References Cited

PUBLICATIONS

Gharbaran et al. (Fibroblast growth factor-2 (FGF2) and syndecan-1 (SDC1) are potential biomarkers for putative circulating CD15+/CD30+ cells in poor outcome Hodgkin lymphoma patients, J Hematol Oncol. Aug. 29, 2013;6:62).*
Vassilakopoulos et al. (Serum Levels of Soluble Syndecan-1 in Hodgkin's Lymphoma, Anticancer Res. Nov.-Dec. 2005;25(6C):4743-6).*
Kowalska et al. (Serum VEGF and bFGF levels in patients with Hodgkin's lymphoma, NOWOTWORY Journal of Oncology, vol. 57, No. 4, 179e-182e, Nov. 2007).*
Carbone et al. (Expression Status of BCL-6 and Syndecan-1 Identifies Distinct Histogenetic Subtypes of Hodgkin's Disease, Blood. Oct. 1, 1998;92(7):2220-8).*
Khnykin et al. (The expression of fibroblast growth factors and their receptors in Hodgkin's lymphoma, J Pathol. Feb. 2006;208(3):431-8).*
Campos et al. (Matrix Metalloproteinase-9 Expression by Hodgkin-Reed-Sternberg Cells is Associated With Reduced Overall Survival in Young Adult Patients With Classical Hodgkin Lymphoma, PLoS One. 2013; 8(9): e74793, Published online Sep. 24, 2013).*
Newcome et al. (Transforming growth factor β1 messenger RNA in Reed-Sternberg cells in nodular sclerosing Hodgkin's disease, Journal of clinical pathology, 48(2):160-163, Feb. 1, 1995).*
Cozen W., et al., "A genome-wide meta-analysis of nodular sclerosing hodgkin lymphoma identifies rish loci at Sp21.32", Blood, 2012, vol. 19, pp. 469-475, www.bloodjournal.org.
Dancey J.E., et al., "The genetic basis for cancer treatment decisions", Cell, 2012, vol. 148, pp. 409-420, Elsevier, Inc.
Enciso-Mora V, et al., A genome-wide association of hodgkin lymphoma identifies new susceptibility loci at 2p16.1 (REL), 8q24.21, and 10p14 (GATA3), Nat Genet., 20101, vol. 42, pp. 1126-1130, Europe PMC Funders Group.
Gharbaran R, et al., "Fibroblast growth factor-2(FGF2) and syndecan-1 (SDC1) are potential biomarkers for putative circulating CD15+/CD30+cells in poor outcome hodgkin lymphoma patients", Journal of Hematology & Oncology, 2013, pp. 1-32.
Goldin L.R., et al., "Familial aggregation of hodgkin lymphoma and related tumors" Cancer, 2004, vol. 100, pp. 1092-1098, Wiley InterScience.
Harty L.C., "HLA-DR, HLA-DQ, and tap genes in familial hodgkin disease", Blood, 2002, vol. 99, pp. 690-693, www.bloodjournal.org.
Hasenclever D, et al., "A prognostic score for advanced hodgkin's disease", The New England Journal of Medicine, 1998, vol. 339, pp. 1506-1514, Massachusetts Medical Society.
Hjalgrim H., et al., "Characteristics of hodgkin's lymphoma after infectious mononucleosis", The New England Journal of Medicine, 2003, vol. 349, pp. 1324-1332, www.nejm.org.
Kronenberg M, et al., "Regulation of immunity by self-reactive T cells", Nature, 2005, vol. 435, pp. 598-604, Nature Publishing Group.

(Continued)

*Primary Examiner* — Aaron Priest
(74) *Attorney, Agent, or Firm* — Chiesa Shahinian & Giantomasi PC

(57) ABSTRACT

The described invention comprises methods for predicting recurrence of Hodgkin Lymphoma (HL) and poor clinical outcome in a Hodgkin Lymphoma (HL) subject. The methods comprise providing a sample from the HL subject and a sample from a good clinical outcome control subject; isolating total RNA comprising Fibroblast Growth Factor-2 (FGF2) and Syndecan-1 (SDC1) RNA from the sample from the HL subject and from the sample from the good clinical outcome control subject; amplifying the total RNA; measuring a level of expression of the FGF2 and the SDC1 RNA in the HL subject and in the good clinical outcome control subject; and comparing the level of expression of the FGF2 and the SDC1 RNA expressed by the HL subject with the level of expression of the FGF2 and the SDC1 RNA expressed by the good clinical outcome control subject. An increased level of expression of the FGF2 RNA and the SDC1 RNA expressed by the HL subject compared to the level of expression of the FGF2 RNA and the SDC1 RNA expressed by the good clinical outcome control subject is indicative of recurrence of HL or poor clinical outcome for the HL subject. The described invention further comprises a method of detecting evidence of metastatic Hodgkin lymphoma in a Hodgkin Lymphoma (HL) subject by measuring an increased level of expression of CD30, FGF2 and SDC1 RNA in an HL subject compared to a good clinical outcome control subject.

11 Claims, 5 Drawing Sheets

(56) References Cited

PUBLICATIONS

Kuruvilla J, et al., "How i treat relapsed and refractory hodgkin lymphoma", Blood, 2011, vol. 117, pp. 4028-4217, The American Society of Hematology.

Kwabi-Addo B, et al., "The role of fibroblast growth factors and their receptors in prostate cancer" Endocrine-Related Cancer, 2004, vol. 11, pp. 709-724, Society for Endocrinology.

Mack T.M., et al., "Concordance for hodgkin's disease in identical twins suggesting genetic susceptibility to the yound-adult form of the disease", The New England Journal of Medicine, 1995, vol. 332, pp. 414-418, Massachusetts Medical Society.

Meyer R.M., et al., "EBV DNA: a hodgkin lymphoma biomarker", Blood, 2013, vol. 121, pp. 3541-3542, www.bloodjurnal.org.

Pallesen G., "Expression of epstein-barr virus latent gene products in tumour cells of hodgkins disease", Lancet, 1991, vol. 337, pp. 1-4.

Staal; S.P., et al., "A survey of epstein-barr virus DNA in lymphoid tissue: Frequent detection in hodgkins diease", A.J.C.P., 1989, vol. 91, pp. 1-5, John Hopkins Oncology Center.

Steidl C., et al., "Molecular pathogenesis of hodgkin's lymphoma: Increasing evidence of the importance of the microenvironment", Journal of Clinical Oncology, 2011, vol. 29, pp. 1812-1826, American Society of Clinical Oncology.

Taams L.S., et al., Human angergic/suppresive CD4+CD25+T cells: a highly differentiated and apoptosis-prone population, Eur. J. Immunol., 2001, vol. 31, pp. 1122-1131, Wiley-VCH Verlag GmbH., Weinheim.

Thomas R.K., et al., "Part;1 Hodgkin's lymphoma-molecular biology of hodgkin and reed-sternberg cells", The Lancet—Oncololgy, vol. 5, 2004, pp. 11-18, http://oncology.thelancet.com.

Weiss L.M., et al., "Rapid Communication: Epstein-Barr Virus and Hodgkin's Disease", American Journal of Pathology, 1991, vol. 139, pp. 1259-1265, American Association of Pathologists.

Schwartz R.H., "T cell antegy", Annu. Rev. Immunol, 2003, vol. 21, pp. 305-334, Laboratory of Cellular and Molecular Immunology, Bethesda, MD.

Re D., et al., "Molecular pathogenesis of hodgkin's lymphoma" Journal of Clinical Oncology, 2005, vol. 23, p. 6379-6385.

Lister T.A., et al., Report of a committee to discuss the evaluation and staging of patients with hodgkins disease: Costwolds meeting:, Journal of Clinical Oncology, 1989, vol. 7, pp. 1630-1636, The American Society of Clinical Oncololgy.

\* cited by examiner

FIBROBLAST GROWTH FACTOR-2 (FGF2) AND SYNDECAN-1 (SDC1) AS BIOMARKERS FOR POOR OUTCOME HODGKIN LYMPHOMA PATIENTS

CROSS-REFERENCE TO RELATED APPLICATIONS

This application claims the benefit of priority to provisional application No. 61/949,629 (filed Mar. 7, 2014), the entire content of which is incorporated by reference herein.

FIELD OF THE INVENTION

The described invention generally relates to Hodgkin Lymphoma (HL).

BACKGROUND

Hodgkin lymphoma (formerly, Hodgkin disease) is a potentially curable lymphoma with distinct histology, biologic behavior, and clinical characteristics. The disease is defined in terms of its microscopic appearance (histology) and the expression of cell surface markers (immunophenotype).

There are 5 types of Hodgkin lymphoma classified by the World Health Organization (WHO) (Jaffe, E S, et al Eds. World Health Organization Classification of Tumours: Pathology and Genetics of Tumours of Haematopoietic and Lymphoid Tissues. Lyon France: IARC Press; 2001). Nodular sclerosing, mixed cellularity, lymphocyte depleted, and lymphocyte rich are the 4 types referred to as classical Hodgkin lymphoma (cHL). The fifth type, nodular lymphocyte-predominant Hodgkin lymphoma (NLPHL), is a distinct entity with unique clinical features and a different treatment paradigm.

Classical HL (cHL) is a monoclonal lymphoid neoplasm that in almost all instances appears to be derived from post-germinal center B cells. The immunohistochemical (IHC) hallmark of HL tumor cells is CD30 antigen expression. The morphological phenotype of cHL comprises an unusually small number (<2%) of mononuclear Hodgkin (H) cells and multinucleated Reed-Sternberg (RS) cells residing in an extensive inflammatory background, which is mostly composed of T cells, histocytes, eosinophils, plasma cells, and macrophages. This inflammatory background in the tumor microenvironment is maintained by Hodgkin's and Reed-Sternberg cell (HRS)-derived chemokines and cytokines that recruit the tumor microenvironment cellular components. The composition of the tumor microenvironment or the molecular phenotype of the HRS cells, or both, is thought to determine the relative aggressiveness of cHL at an individual level. (Gharbaran et al., "Fibroblast growth factor-2 (FGF2) and syndecan-1 (SDC1) are potential biomarkers for putative circulating CD15+/CD30+ cells in poor outcome Hodgkin Lymphoma patients." Journal of Hematology & Oncology, 2013, 6:62)

In classical Hodgkin lymphoma, the neoplastic cell is the Reed-Sternberg cell, which is a large, abnormal lymphocyte that may contain more than one nucleus. (Thomas, R K et al, Part I: Hodgkin's lymphoma-molecular biology of Hodgkin and Reed-Sternberg cells. Lancet Oncol. January 2004; 5(1): 11-18; Re, D, et al, Molecular pathogenesis of Hodgkin's lymphoma. J. Clin. Oncol. Sep. 10, 2005; 23(26): 6379-86) Reed-Sternberg cells comprise only 1-2% of the total tumor cell mass. The remainder is composed of a variety of reactive, mixed inflammatory cells consisting of lymphocytes, plasma cells, neutrophils, eosinophils, and histiocytes. Reed-Sternberg cells consistently express CD30 (Ki-1) and CD15 (Leu-M1) antigens. CD30 is a marker of lymphocyte activation expressed by reactive and malignant lymphoid cells. CD15 is a marker of late granulocytes, monocytes, and activated T-cells not normally expressed by cells of B lineage.

Nodular Sclerosing Hodgkin Lymphoma (NSHL)

In NSHL, which constitutes 60-80% of all cases of Hodgkin lymphoma, the morphology shows a nodular pattern. Broad bands of fibrosis divide the node into nodules, and the capsule is thickened. The characteristic cell is the lacunar-type Reed-Sternberg cell, which has a monolobated or multilobated nucleus, a small nucleolus, and abundant pale cytoplasm.

Mixed-Cellularity Hodgkin Lymphoma (MCHL)

In MCHL, which constitutes 15-30% of cases, the infiltrate is usually diffuse. Reed-Sternberg cells are of the classical type (large, with bilobate, double or multiple nuclei, and a large, eosinophilic nucleolus). MCHL commonly affects the abdominal lymph nodes and spleen. Patients with this histology typically have advanced-stage disease with systemic symptoms. MCHL is the histologic type most commonly observed in patients with human immunodeficiency virus (HIV) infection.

Lymphocyte-Depleted Hodgkin Lymphoma (LDHL)

LDHL constitutes less than 1% of Hodgkin lymphoma cases. The infiltrate in LDHL is diffuse and often appears hypocellular. Large numbers of Reed-Sternberg cells and bizarre sarcomatous variants are present.

LDHL is associated with older age and HIV-positive status. Patients usually present with advanced-stage disease. Epstein-Barr virus (EBV) proteins are expressed in many of these tumors. Many cases of LDHL diagnosed in the past were actually non-Hodgkin lymphomas, often of the anaplastic large-cell type.

Lymphocyte-Rich Classical Hodgkin Lymphoma (LRHL)

LRHL constitutes 5% of cases. In LRHL, Reed-Sternberg cells of the classical or lacunar type are observed, with a background infiltrate of lymphocytes. It requires immunohistochemical diagnosis. Some cases may have a nodular pattern. Clinically, the presentation and survival patterns are similar to those for MCHL.

Nodular Lymphocyte-Predominant Hodgkin Lymphoma

Nodular lymphocyte-predominant Hodgkin lymphoma (NLPHL) constitutes 5% of Hodgkin lymphoma cases. It is a distinct clinical entity and is not considered part of the classical Hodgkin lymphoma. Typical Reed-Sternberg cells are either infrequent or absent in NLPHL. Instead, lymphocytic and histiocytic (L&H) cells, or "popcorn cells" (their nuclei resemble an exploded kernel of corn), are seen within a background of inflammatory cells, which are predominantly benign lymphocytes. Unlike Reed-Sternberg cells, L&H cells are positive for B-cell antigens, such as CD20, and are negative for CD15 and CD30. A diagnosis of NLPHL needs to be supported by immunohistochemical studies, because it can appear similar to LRHL or even some non-Hodgkin lymphomas.

Etiology

The etiology of Hodgkin lymphoma is unknown. Infectious agents, particularly Epstein-Ban virus (EBV), may be involved in the pathogenesis. Depending on the study, data show that up to 30% of cases of classical Hodgkin lymphoma may be positive for EBV proteins. (Staal, S P, et al, A survey of Epstein-Barr virus DNA in lymphoid tissue. Frequent detection in Hodgkin's disease. Am. J. Clin. Pathol. January 1989; 91(1): 1-5). In addition, a case control study supports an increased risk of classical Hodgkin lymphoma after EBV infection, with a risk of approximately 1 in 1000 cases. (Hjalgrim, H., et al, Characteristics of Hodgkin's lymphoma after infectious mononucleosis. N. Eng. J. Med. Oct. 2, 2003; 349 (14): 1324-32) The incidence of EBV positivity varies with subtype. Nodular lymphocyte-predominant Hodgkin lymphoma (NLPHL) rarely expresses EBV proteins (Weiss, L M, et al, Epstein-Barr virus and Hodgkin's disease. A correlative in situ hybridization and polymerase chain reaction study. Am. J. Pathol. December 1991; 139(6): 1259-65), whereas in classical Hodgkin lymphoma, EBV positivity is most common in the mixed-cellularity variant. (Pallesen, G et al., Expression of Epstein-Ban virus latent gene products in tumour cells of Hodgkin's disease. Lancet: Feb. 9, 1991; 337 (8737): 320-322). However, the exact mechanism by which EBV can lead to Hodgkin lymphoma is not known.

HIV-positive patients also have a higher incidence of Hodgkin lymphoma compared to HIV-negative patients. However, Hodgkin lymphoma is not considered an AIDS-defining neoplasm.

Genetic predisposition plays a role in the pathogenesis of Hodgkin lymphoma. Approximately 1% of patients with Hodgkin lymphoma have a family history of the disease, and siblings of an affected individual have a 3- to 7-fold increased risk of developing the disease. (Goldin, L R et al, Familial aggregation of Hodgkin lymphoma and related tumors Cancer, May 1, 2004 100(9): 1902-1908). Most evidence for a genetic etiology has been established in the distinct subtype of nonsclerosing Hodgkin lymphoma (NSHL). NSHL has been shown to be one of the most heritable types of neoplasm with a 100-fold increased risk in identical twins. Harty, L C et al, HLA-DR, HLA-DQ and TAP genes in familial Hodgkin disease. Blood, Jan. 15, 2002; 99(2): 690-93; Mack, T M et al, Concordance for Hodgkin's disease in identical twins suggesting genetic susceptibility to the young-adult form of the disease. N. Engl. J. Med. Feb. 16, 1995; 332(7): 413-18).

There is evidence that NSHL may result from an atypical immune response to a virus or other trigger, and that an atypical immunogenic response is involved. (Mueller, N E and Grufferman, S. Hodgkin lymphoma. InSchottenfield, D., Fraumeni, J F, Jr. Eds. Cancer Epidemiology and Prevention. New York, N.Y.: Oxford Univ. Press; 2006: 872-97). For decades, there have been known specific human leukocyte antigen (HLA) class II genotypes, including HLA-DRB1 and HLA-DQB1, that are associated with NSHL, and this has been confirmed by genome-wide association studies. (Cozen, W et al, A genome-wide meta-analysis of nodular sclerosing Hodgkin lymphoma identifies risk loci at 6p21.32. Blood. Jan. 12, 2012; 119 (2): 469-75; Enciso-Mora, V et al, A genome-wide association study of Hodgkin's lymphoma identifies new susceptibility loci at 2p16.1 (REL), 8q24.21 and 10p14 (GATA3). Natl Genet. December 2010: 42(12): 1126-30) Several single-nucleotide polymorphisms in the 6p21.32 region, which is rich in genes associated with immune function, have also been associated with NSHL risk. (Cozen, W et al, A genome-wide meta-analysis of nodular sclerosing Hodgkin lymphoma identifies risk loci at 6p21.32. Blood. Jan. 12, 2012; 119 (2): 469-75).

The Ann Arbor classification has been used to describe the stage of Hodgkin disease at initial presentation. This classification was modified to modify the classification in light of experience and new techniques for evaluating disease. As a result, it was recommended that computed tomography (CT) was included as a technique for evaluating intrathoracic and infradiaphragmatic lymph nodes; the criteria for clinical involvement of the spleen and liver be modified to include evidence of focal defects with two imaging techniques, and that abnormalities of liver function be ignored; that the suffix "X" be introduced to designate bulky disease (greater than 10 cm maximum dimension); and that a new category of response to therapy, unconfirmed/uncertain complete remission [CR[u]] be introduced to accommodate the difficulty of persistent radiological abnormalities of uncertain significance. (Lister, T A, et al, J Clin. Oncol. November 1989; 7(11): 1630-36). The Cotswolds modified Ann Arbor staging system for Hodgkin lymphoma is shown in Table 1. Regions of lymph node involvement are denoted by an E designation. The A and B designations denote the absence or presence of symptoms, respectively; the presence of symptoms correlates with treatment response.

TABLE 1

The Cotswolds modified Ann Arbor staging system for Hodgkin lymphoma

| Stage | Area of Involvement |
|---|---|
| I | Single lymph node group |
| II | Multiple lymph node groups on same side of diaphragm |
| III | Multiple lymph node groups on both sides of diaphragm |
| IV | Multiple extranodal sites or lymph nodes and extranodal disease |
| X | Bulk >10 cm |
| E | Extranodal extension or single, isolated site of extranodal disease |
| A/B | B symptoms: weight loss >10%, fever, drenching night sweats |

In addition to the stage of the disease, many factors contribute to the likelihood of survival from Hodgkin lymphoma. The following table, which includes data from 3 organizations (the German Study Hodgkin Lymphoma Study Group (GSHG), European Organization for Research and Treatment of Cancer (EORTC), and the National Cancer Institute of Canada (NCIC)), shows examples of unfavorable risk factors for stages I and II.

TABLE 2

Unfavorable Risk Factors for Stages I and II Hodgkin Lymphoma

| Risk Factor | GSHG | EORTC | NCIC |
|---|---|---|---|
| Age | | ≥50 y | ≥40 y |
| Histology | | MC or LD | |
| ESR or B symptoms | >50 if A or >30 if B | >50 if A or >30 if B | >50 or any B symptoms |
| Mediastinal mass* | MMR > 0.33 | MMR > 0.35 | MMR > 0.33 or > 10 cm |
| Number of nodal sites | >2 | >3 | >3 |
| Extranodal lesions | Any | | |

*Mediastinal mass is measured on chest x-ray by the mediastinal mass ratio (MMR), which is defined by the following: maximum width of mass/maximum intrathoracic diameter. Constitutional symptoms, e.g., unexplained weight loss (>10% of total body weight), unexplained fever, night sweats, collectively are known as B symptoms.
ESR = erythrocyte sedimentation rate; LD = lymphocyte depletion; MC = mixed cellularity.

TABLE 3

Stage Distribution and 5-Year Relative Survival by Stage at Diagnosis for All Races and Both Sexes: 2002-2008

| Stage at Diagnosis | Stage Distribution, % | 5-year Relative Survival, % |
|---|---|---|
| Localized (confined to primary site) | 18 | 90.0 |
| Regional (spread to regional lymph nodes) | 41 | 91.0 |
| Distant (cancer has metastasized) | 37 | 75.7 |

Source: National Cancer Institute. SEER stat fact sheets: Hodgkin lymphoma. Available at: http://www.seer.cancer.gov/statfacts/html/hodg.html. Accessed: Feb. 20, 2014

Based on these criteria, patients are classified as follows:

Early-stage favorable HL (includes patients with stage I or II HL and no risk factors by GSHG/EORTC or NCIC)

Early-stage unfavorable HL (includes patients with stage I and II HL and one or more risk factors)

Advanced-stage HL (includes patients with stages IIB, III, and IV)

Patients with advanced disease are further risk stratified using the International Prognostic Score (IPS), which includes the following risk factors (for each present factor, the patient receives 1 point) (Hasenclever, D and Diehl, V, "A Prognostic score for advanced Hodgkin's disease. Intl prognostic factors project on advanced Hodgkin's disease, N. Eng. J. Med. November 1998; 339 (21): 1506-14):

Albumin <4 g/dL

Hemoglobin <10.5 g/dL

Male

Age ≥45 y

Stage IV disease

Leukocytosis: white cell count (WBC)>15,000/µL

Lymphopenia: lymphocyte count <8% of WBC count and/or absolute lymphocyte count <600 cells/µL Based on the IPS score, patients with advanced disease can be categorized as follows:

Good risk (IPS 0-1)

Fair risk (IPS 2-3)

Poor risk (IPS 4-7)

Although the International Prognostic Score was introduced to improve the risk stratification of patients, its applicability is limited for predicting high risk classical HL patients, regardless of clinical stage.

Up to 20% of Hodgkin lymphoma (HL) patients are either refractory to treatment (primary refractory) or experience relapse within four years (early relapse) of achieving complete remission (CR); this figure includes patients who experience progressive disease and patients with a particularly poor prognosis for other reasons. Only half of HL patients survive for two years if front line therapy fails, and autologous hematopoietic stem-cell transplant (ASCT) is only 50% curative. While patients in this group may benefit from analysis of the tumor-associated macrophage marker CD68, which can be used to predict adverse outcomes of cHL, the prediction is controversial.

The treatment of early-stage Hodgkin lymphoma (HL) has improved significantly, with treatment failure occurring in approximately 10% of patients. Although the therapy of advanced-stage HL has also improved, up to 10% of patients with advanced-stage HL will not achieve complete remission (CR), and 20%-30% of responding patients subsequently relapse after treatment. Salvage chemotherapy followed by autologous stem cell transplantation (ASCT) is the treatment of choice in patients with relapsed HL or if the disease is refractory to initial chemotherapy. (Kuruvilla, J. et al., Blood, 2011; 117(16): 4208-4217, at 4208.)

Prognostic factors have been identified in cohorts of patients with relapsed or refractory HL (RR-HL) who have undergone subsequent salvage chemotherapy and ASCT (summarized in Table 4). Time to relapse after initial therapy, advanced stage at relapse, and poor performance status consistently have been demonstrated to be predictors of poor outcome. (Id.)

TABLE 4

Poor prognostic factors in relapsed or refractory Hodgkin lymphoma

| Patient group | Factor |
|---|---|
| Relapsed | Time to relapse <1 year |
| | Stage III-IV |
| | Anemia |
| | B symptoms (e.g., fever, weight loss, and night sweats)[1] |
| | Poor performance status |
| Refractory | Poor performance status |
| | Age >50 years |
| | Failure to attain a temporary remission |
| | B symptoms (e.g., fever, weight loss, and night sweats) |
| | Stage III-IV |
| Autologous stem cell transplant | Previously untreated relapse |
| | Response to chemotherapy |
| | Low serum albumin |
| | Anemia |
| | Age |
| | Lympocytopenia |
| | B symptoms (e.g., fever, weight loss, and night sweats) |
| | Extranodal disease |
| | Time to relapse <1 year |
| | Disease status at autologous stem cell transplant |
| | Disease relapse in previous radiation field |

[1] Kurzrock, R. et al., "Serum interleukin 6 levels are elevated in lymphoma patients and correlate with survival in advanced Hodgkin's Disease and with B Symptoms." Cancer Research, 1993; 53: 2118-2122, at 2122.
(Table reproduced from: Kuruvilla, J. et al., Blood, 2011; 117 (16): 4208-4217, at 4208.)

To date, there are no reliable biomarkers to predict high risk, unfavorable, poor outcome of Hodgkin's lymphoma (HL) at the time of diagnosis or as a baseline marker. Such biomarkers would be useful (1) to provide better alternative treatment options, for example, customized/personalized dosing regimens, or (2) to spare patients from a course of treatment that has no hope of working from the onset.

Molecular abnormalities that define a disease process epitomize opportunities associated with biomarkers because these are not only a diagnostic criterion of the disease, but also are targets for therapeutic intervention and serve as quantitative measures of the disease process which can be used to monitor therapeutic response in individuals. However, such biomarkers are rare (Meyer R M, Blood May 2, 2013 vol. 121 no. 18 3541-3542). The list of cancer-related biomarkers that have predictive properties is short (Meyer R M, Blood May 2, 2013 vol. 121 no. 18 3541-3542; Dancey J E et al., Cell 2012; 148(3): 409-420; Hasenclever D. et al., N Engl J Med 1998; 339(21): 1506-1514). Those currently in use have a common feature: all either represent a molecular entity that defines the disease or are intimately involved in the mechanism of action of the targeted therapy as either a cellular membrane or intracellular signaling protein that may serve as the therapeutic agent's binding site and that affects the downstream molecular machinery that ultimately determines cancer survival (Meyer R M, Blood May 2, 2013 vol. 121 no. 18 3541-3542).

Thus far, none of the prognostic biomarkers associated with secondary biologic events, including those identified in Hodgkin's lymphoma (HL), have demonstrated predicative capacities (Steidl C. et al., J Clin Oncol 2011; 29(14): 1812-1826). For example, although CD68, a type I transmembrane protein present on monocytes, macrophages, osteoclasts, mast cells, cytoplasmic granules, activated platelets, and large lymphocytes, has been used as a biomarker for HL (See, Steidl C. et al., J Clin Oncol 2011; 29(14): 1812-1826; Table 2 at page 1818), its expression is not limited to HL, i.e., CD68 is not only expressed in anaplastic lymphomas, but is also expressed in neuroma Schwann cells, in nerves undergoing wallerian degeneration, in myeloid cell tumors and epithelial tumors.

The described invention identifies biomarkers useful in the detection of Hodgkin Lymphoma patients with poor clinical outcome, in the detection of recurrent Hodgkin lymphoma, and in the detection of evidence of metastatic Hodgkin lymphoma.

The term "FGF gene family" as used herein refers to a gene family consists of at least 23 different genes encoding related polypeptides. FGFs are expressed in almost all tissues and play important roles in a variety of normal and pathological processes, including development, wound healing and neoplastic transformation. FGFs have a broad range of biological activities that can play a role in tumorigenesis, for example, they are mitogenic for many cell types, both epithelial and mesenchymal; some FGFs, like FGF2, have potent angiogenic activity and have been implicated as promoters of tumor angiogenesis; they have been shown to increase the motility and invasiveness of a variety of cell types; and FGFs can inhibit cell death in the appropriate context. (Kwabi-Addo et al., "The role of fibroblast growth factors and their receptors in prostate cancer." Endocrine-Related Cancer, 2004, 11:709-724, at 709-710.)

Increased Syndecan-1 (SDC-1) expression in stromal fibroblasts is observed in several carcinomas, such as those of the breast, stomach, and thyroid. In a xenograft model of human breast carcinoma cells and SDC-1-transfected fibroblasts implantation into mice, stromal SDC-1 expression was associated with significantly elevated microvessel density and larger vessel area. Expression of SDC-1 in stromal fibroblasts of human breast carcinomas also correlated significantly with high microvessel density and larger vessel area. These findings raise the possibility that SDC-1 in the reactive stroma may sequester pro-angiogenic factors and increase the local concentration of these factors to promote angiogenesis (Teng et al., "Molecular functions of syndecan-1 in disease." Matrix Biol. 2012; 31(1):3-16.).

Tumor angiogenesis generates new vascular beds that provide nutrients and oxygen for the highly metabolic tumor mass. SDC-1 can bind to pro-angiogenic factors like FGF-2 and VEGF, and subsequently present these factors to their respective receptors on endothelial cells to initiate endothelial invasion and budding. The broader functional implications of SDC-1 in angiogenesis may also be to allow soluble SDC-1 ectodomains with bound pro-angiogenic factors to foster angiogenesis at premetastatic niches. For example, in myeloma, shedding of SDC-1 ectodomains by heparanase facilitated endothelial invasion and subsequent angiogenesis. Heparanase also upregulated HGF and VEGF in myeloma cells, and SDC-1 ectodomains bound to VEGF and presented VEGF to endothelial cells. Binding of SDC-1 ectodomains to αvβ3 and αvβ5 integrins is apparently necessary for its pro-angiogenic function, as a short inhibitory peptide that mimics the SDC-1 ectodomain endothelial cell invasion as well as tumor growth in vivo. (Teng et al., "Molecular functions of syndecan-1 in disease." Matrix Biol. 2012; 31(1):3-16).

SUMMARY OF THE INVENTION

According to one aspect, the described invention provides a method for predicting recurrence of Hodgkin Lymphoma (HL) in a subject treated with a first treatment regimen comprising: (a) providing a sample from the subject and a sample from a good clinical outcome control subject; (b) isolating total RNA comprising Fibroblast Growth Factor-2 (FGF2) and Syndecan-1 (SDC1) RNA from the sample from the subject and from the sample from the good clinical outcome control subject; (c) amplifying the total RNA from step (b); (d) measuring a level of expression of the FGF2 and the SDC1 RNA in the subject and in the good clinical outcome control subject; (e) comparing the level of expression of the FGF2 and the SDC1 RNA in step (d) expressed by the subject with the level of expression of the FGF2 and the SDC1 RNA in step (d) expressed by the good clinical outcome control subject, wherein an increased level of expression of the FGF2 RNA and the SDC1 RNA expressed by the subject compared to the level of expression of the FGF2 RNA and the SDC1 RNA expressed by the good clinical outcome control subject is indicative of recurrence of HL in the subject; (f) predicting recurrence of Hodgkin Lymphoma (HL) in the subject based on step (e); and (g) treating the subject with a second treatment regimen effective to treat the recurrence of HL.

According to one embodiment, the sample is selected from the group consisting of a tumor biopsy, blood, a lymph node and peripheral blood leukocytes (PBL).

According to one embodiment, amplifying is performed by Reverse Transcriptase-Polymerase Chain Reaction (RT-PCR).

According to one embodiment, the method for predicting recurrence of Hodgkin Lymphoma (HL) in a subject treated with a first treatment regimen further comprises: (d') measuring a level of expression of TGFβ1 and MMP9 RNA in the subject and in the good clinical outcome control subject; (e') comparing the level of expression of the TGFβ1 and the MMP9 RNA in step (d') expressed by the subject with the level of expression of the TGFβ1 and the MMP9 RNA in step (d') expressed by the good clinical outcome control subject, wherein an increased level of expression of the TGFβ1 RNA and the MMP9 RNA expressed by the subject compared to the level of expression of the TGFβ1 RNA and the MMP9 RNA expressed by the good clinical outcome control subject is indicative of recurrence of HL in the subject.

According to another aspect, the described invention provides a method for predicting poor clinical outcome in a Hodgkin Lymphoma (HL) subject comprising: (a) providing a sample from the HL subject and a sample from a good clinical outcome control subject; (b) isolating total RNA comprising Fibroblast Growth Factor-2 (FGF2) and Syndecan-1 (SDC1) RNA from the sample from the HL subject and from the sample from the good clinical outcome control subject; (c) amplifying the total RNA from step (b); (d) measuring a level of expression of the FGF2 and the SDC1 RNA in the HL subject and in the good clinical outcome control subject; (e) comparing the level of expression of the FGF2 and the SDC1 RNA in step (d) expressed by the HL subject with the level of expression of the FGF2 and the SDC1 RNA in step (d) expressed by the good clinical outcome control subject, wherein an increased level of expression of the FGF2 RNA and the SDC1 RNA expressed by the HL subject compared to the level of expression of the FGF2 RNA and the SDC1 RNA expressed by the good clinical outcome control subject is indicative of poor clinical outcome for the HL subject; (f) predicting poor clinical outcome for the HL subject based on step (e); and (g) replacing a treatment regimen likely to be ineffective with a replacement treatment regimen effective to maintain the subject's quality of life.

According to one embodiment, the sample is selected from the group consisting of a tumor biopsy, blood, a lymph node and peripheral blood leukocytes (PBL).

According to one embodiment, amplifying is performed by Reverse Transcriptase-Polymerase Chain Reaction (RT-PCR).

According to one embodiment, the method for predicting poor clinical outcome in a Hodgkin Lymphoma (HL) subject further comprises: (d') measuring a level of expression of TGFβ1 and MMP9 RNA in the subject and in the good clinical outcome control subject; (e') comparing the level of expression of the TGFβ1 and the MMP9 RNA in step (d') expressed by the subject with the level of expression of the TGFβ1 and the MMP9 RNA in step (d') expressed by the good clinical outcome control subject, wherein an increased level of expression of the TGFβ1 RNA and the MMP9 RNA expressed by the subject compared to the level of expression of the TGFβ1 RNA and the MMP9 RNA expressed by the good clinical outcome control subject is indicative of poor clinical outcome for the HL subject.

According to another aspect, the described invention provides a method of detecting evidence of metastatic Hodgkin lymphoma in a Hodgkin Lymphoma (HL) subject comprising: (a) providing a peripheral blood leukocyte (PBL) sample from the HL subject and a PBL sample from a good clinical outcome control subject; (b) isolating total RNA comprising CD30, Fibroblast Growth Factor-2 (FGF2) and Syndecan-1 (SDC1) RNA from the PBL sample from the HL subject and from the PBL sample from the good clinical outcome control subject; (c) amplifying the total RNA from step (b); (d) measuring a level of expression of the CD30, the FGF2 and the SDC1 RNA in the HL subject and in the good clinical outcome control subject; (e) comparing the level of expression of the CD30, the FGF2 and the SDC1 RNA in step (d) expressed by the HL subject with the level of expression of the CD30, the FGF2 and the SDC1 RNA in step (d) expressed by the good clinical outcome control subject, wherein an increased level of expression of the CD30, the FGF2 and the SDC1 RNA expressed by the HL subject compared to the level of expression of the CD30, the FGF2 and the SDC1 RNA expressed by the good clinical outcome control subject is indicative of a metastasis in the HL subject; and (f) detecting evidence of metastatic Hodgkin lymphoma in the HL subject based on step (e), and (g) implementing an appropriate treatment plan.

According to one embodiment, the amplifying is performed by Reverse Transcriptase-Polymerase Chain Reaction (RT-PCR).

According to one embodiment, the method of detecting metastatic Hodgkin lymphoma in a Hodgkin Lymphoma (HL) subject further comprises: (d') measuring a level of expression of CD15 RNA in the HL subject and in the good clinical outcome control subject; (e') comparing the level of expression of the CD15 RNA in step (d') expressed by the HL subject with the level of expression of the CD15 RNA in step (d') expressed by the good clinical outcome control subject, wherein an increased level of expression of the CD15 RNA expressed by the HL subject compared to the level of expression of the CD15 RNA expressed by the good clinical outcome control subject is indicative of a poor clinical outcome for the HL subject.

According to one embodiment, the method of detecting evidence of metastatic Hodgkin lymphoma in a Hodgkin Lymphoma (HL) subject further comprises: (d') measuring a level of expression of TGFβ1 and MMP9 RNA in the HL subject and in the good clinical outcome control subject; (e') comparing the level of expression of the TGFβ1 and the MMP9 RNA in step (d') expressed by the HL subject with the level of expression of the TGFβ1 and the MMP9 RNA in step (d') expressed by the good clinical outcome control subject, wherein an increased level of expression of the TGFβ1 RNA and the MMP9 RNA expressed by the HL subject compared to the level of expression of the TGFβ1 RNA and the MMP9 RNA expressed by the good clinical outcome control subject is indicative of metastatic HL in the HL subject.

According to one embodiment, the evidence of metastatic Hodgkin lymphoma comprises a circulating CD30+ cell with an FGF2+/SDC1+ immunophenotype. According to another embodiment, the circulating CD30+ cell with the FGF2+/SDC1+ immunophenotype is a Hodgkin Lymphoma and Reed-Sternberg (HRS) cell.

BRIEF DESCRIPTION OF THE DRAWINGS

For a more complete understanding of the present disclosure, reference is made to the following detailed description of exemplary embodiments considered in conjunction with the accompanying drawings.

DETAILED DESCRIPTION OF THE INVENTION

Figure 1:
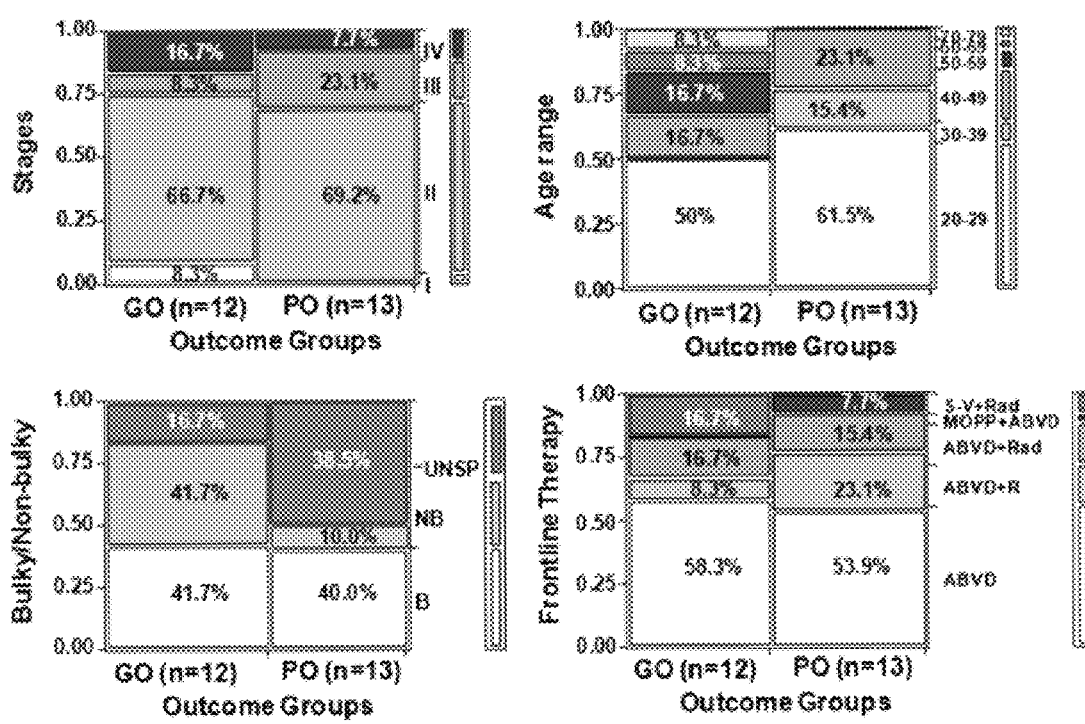
FIG. 1 shows lack of association between clinical outcome and tumor staging, age, bulkiness, or frontline therapies and the overexpression of FGF2 and SDC1 by HL cell lines. Contingency analysis was performed against major clinical characteristics (y-axis, right column) including tumor stage (p>0.4), age group (p>0.11), bulkiness of the disease (p>0.18), and frontline therapies used (p>0.27) for HL patients with good outcome (GO) versus poor outcome (PO) (x-axis). The percentage of each clinical characteristic within each group is indicated.

The described invention can be better understood from the following description of exemplary embodiments, taken in conjunction with the accompanying figures and drawings. It should be apparent to those skilled in the art that the described embodiments of the described invention provided herein are merely exemplary and illustrative and not limiting.

DEFINITIONS

Various terms used throughout this specification shall have the definitions set out herein.

"Activation" or "lymphocyte activation" refers to stimulation of lymphocytes by specific antigens, nonspecific mitogens, or allogeneic cells resulting in synthesis of RNA, protein and DNA and production of lymphokines; it is followed by proliferation and differentiation of various effector and memory cells. For example, a mature B cell can be activated by an encounter with an antigen that expresses epitopes that are recognized by its cell surface immunoglobulin Ig). The activation process may be a direct one, dependent on cross-linkage of membrane Ig molecules by the antigen (cross-linkage-dependent B cell activation) or an indirect one, occurring most efficiently in the context of an intimate interaction with a helper T cell ("cognate help process"). T-cell activation is dependent on the interaction of the TCR/CD3 complex with its cognate ligand, a peptide bound in the groove of a class I or class II MHC molecule. The molecular events set in motion by receptor engagement are complex. Among the earliest steps appears to be the activation of tyrosine kinases leading to the tyrosine phosphorylation of a set of substrates that control several signaling pathways. These include a set of adapter proteins that link the TCR to the ras pathway, phospholipase Cγ1, the tyrosine phosphorylation of which increases its catalytic activity and engages the inositol phospholipid metabolic pathway, leading to elevation of intracellular free calcium concentration and activation of protein kinase C, and a series of other enzymes that control cellular growth and differentiation. Full responsiveness of a T cell requires, in addition to receptor engagement, an accessory cell-delivered costimulatory activity, e.g., engagement of CD28 on the T cell by CD80 and/or CD86 on the antigen presenting cell (APC). The soluble product of an activated B lymphocyte is immunoglobulins (antibodies). The soluble product of an activated T lymphocyte is lymphokines.

The term "administering" as used herein includes in vivo administration, as well as administration directly to tissue ex vivo. Generally, compositions can be administered systemically either orally, buccally, parenterally, topically, by inhalation or insufflation (i.e., through the mouth or through the nose), or rectally in dosage unit formulations containing conventional nontoxic pharmaceutically acceptable carriers, adjuvants, and vehicles as desired, or can be locally administered by means such as, but not limited to, injection, implantation, grafting, topical application, or parenterally.

The term "biomarker" (or "biosignature") as used herein refers to a peptide, a protein, a nucleic acid, an antibody, a gene, a metabolite, or any other substance used as an indicator of a biologic state. It is a characteristic that is measured objectively and evaluated as a cellular or molecular indicator of normal biologic processes, pathogenic processes, or pharmacologic responses to a therapeutic intervention. The term "cancer biomarker" (or "cancer biosignature") as used herein refers to a peptide, a protein, a nucleic acid, an antibody, a gene, a metabolite, or any other substance used to detect the predisposition for, or the presence of, primary or metastatic cancer in a subject. According to the descried invention, biomarkers useful in the detection of poor clinical outcome (PO) Hodgkin Lymphoma patients include, but are not limited to, CD15, CD30, FGF2, MMP9, SDC1, TGFβ1 and the like.

The CD system nomenclature commonly used to identify cell markers thus allows cells to be defined based on what molecules are present on their surface. These markers often are used to associate cells with certain immune functions. While using one CD molecule to define populations is uncommon, combining markers has allowed for cell types with very specific definitions within the immune system. There are more than 350 CD molecules identified for humans.

CD molecules are utilized in cell sorting using various methods, including flow cytometry. Cell populations usually are defined using a "+" or a "−" symbol to indicate whether a certain cell fraction expresses ("+") or lacks ("−") a CD molecule. CD molecules are not exclusively markers on the cell surface. Most CD molecules have an important function, although only a small portion of known CD molecules have been characterized. For example, there are over 350 CD molecules for humans identified thus far.

CD4 is a membrane glycoprotein of T lymphocytes that interact with major histocompatibility complex class II antigens and is also a receptor for the human immunodeficiency virus. CD4 functions to initiate or augment the early phase of T-cell activation, and may function as an important mediator of indirect neuronal damage in infectious and immune-mediated diseases of the central nervous system.

CD8 is a type I transmembrane protein found on suppressor (cytotoxic) T cells, some natural killer cells, and most thymocytes that is involved in T-cell antigen recognition. CD8 is expressed in some T-cell lymphomas and large granular lymphocyte leukemias.

CD14 is a cell surface protein expressed mainly by macrophages and, to a lesser extent, neutrophil granulocytes. CD14+ cells are monocytes that can differentiate into a host of different cells; for example, differentiation to dendritic cells is promoted by cytokines such as GM-CSF and IL-4. CD14 acts as a co-receptor (along with toll-like receptor (TLR) 4 and lymphocyte antigen 96 (MD-2)) for the detection of bacterial lipopolysaccharide (LPS). CD14 only can bind LPS in the presence of lipopolysaccharide binding protein (LBP).

CD15 (3-fucosyl-N-acetyl-lactosamine; stage specific embryonic antigen 1 (SSEA-1)) is a carbohydrate adhesion molecule that can be expressed on glycoproteins, glycolipids and proteoglycans. CD15 commonly is found on neutrophils and mediates phagocytosis and chemotaxis. CD15 also is found on classical Hodgkin Lymphoma Reed-Sternberg (HRS) cells.

CD19 is a human protein expressed on follicular dendritic cells and B cells. This cell surface molecule assembles with the antigen receptor of B lymphocytes in order to decrease the threshold for antigen receptor-dependent stimulation. It generally is believed that, upon activation, the cytoplasmic tail of CD19 becomes phosphorylated, which allows binding by Src-family kinases and recruitment of phosphoinositide 3 (PI-3) kinases.

CD20 is a non-glycosylated phosphoprotein expressed on the surface of all mature B-cells. Studies suggest that CD20 plays a role in the development and differentiation of B-cells into plasma cells. CD20 is encoded by a member of the membrane-spanning 4A gene family (MS4A). Members of this protein family are characterized by common structural features and display unique expression patterns among hematopoietic cells and nonlymphoid tissues.

CD30 is a type I transmembrane protein present on activated T and B cells that may play a role in cell activation and/or differentiation. CD30 is expressed in Hodgkin disease, some T-cell lymphomas, and anaplastic large cell lymphomas.

CD38 is a multifunctional ectoenzyme expressed on hematopoietic cells, B cells, T cells, Natural Killer cells, monocytes and macrophages. CD38 functions in cell adhesion, signal transduction and calcium signaling.

CD63 (LAMP-3; ME491; MLA1; OMA81H) is a cell surface glycoprotein of the transmembrane 4 superfamily (tetraspanin family). Many of these cell surface receptors have four hydrophobic domains and mediate signal transduction events that play a role in the regulation of cell development, activation, growth and motility. CD63 forms complexes with integrins and may function as a blood platelet activation marker. It generally is believed that the sensitivity and specificity of measuring the upregulation of CD63 alone, or as part of a combination, is not specific enough to serve as a diagnostic marker for the diagnosis of IgE mediated allergy.

CD68 is a type I transmembrane protein present on monocytes, macrophages, osteoclasts, mast cells, cytoplasmic granules, activated platelets, and large lymphocytes. CD68 is expressed in neuroma Schwann cells, in nerves undergoing wallerian degeneration, in myeloid cell tumors, and in anaplastic lymphomas and epithelial tumors.

The term "cDNA" refers to DNA synthesized from a mature mRNA template. cDNA most often is synthesized from mature mRNA using the enzyme reverse transcriptase. The enzyme operates on a single strand of mRNA, generating its complementary DNA based on the pairing of RNA base pairs (A, U, G, C) to their DNA complements (T, A, C, G). There are several methods known for generating cDNA to obtain, for example, eukaryotic cDNA whose introns have been spliced. Generally, these methods incorporate the following steps: a) a eukaryotic cell transcribes the DNA (from genes) into RNA (pre-mRNA); b) the same cell processes the pre-mRNA strands by splicing out introns, and adding a poly-A tail and 5' Methyl-Guanine cap; c) this mixture of mature mRNA strands is extracted from the cell; d) a poly-T oligonucleotide primer is hybridized onto the poly-A tail of the mature mRNA template. (Reverse transcriptase requires this double-stranded segment as a primer to start its operation.); e) reverse transcriptase is added, along with deoxynucleotide triphosphates (A, T, G, C); f) the reverse transcriptase scans the mature mRNA and synthesizes a sequence of DNA that complements the mRNA template. This strand of DNA is complementary DNA.

The term "cell" is used herein to refer to the structural and functional unit of living organisms and is the smallest unit of an organism classified as living.

The term "chemo-exposed" or "chemotherapy exposed" as used herein refers to patients that have received treatment with a chemotherapeutic or chemotherapeutic regimen.

The term "chemo-naïve" or "chemotherapy naïve" as used herein refers to patients who have not received treatment with a chemotherapeutic or chemotherapic regimen.

The term "condition" as used herein, refers to a variety of health states and is meant to include disorders or diseases caused by injury or any underlying mechanism or disorder.

The term "disease" or "disorder" as used herein refers to an impairment of health or a condition of abnormal functioning.

The terms "fibroblast growth factor-2" or "FGF2" are used interchangeably herein to refer to a member of the fibroblast growth factor (FGF) family that binds heparin and possesses broad mitogenic and angiogenic activities. FGF2 has been implicated in diverse biological processes, such as limb and nervous system development, wound healing, and tumor growth. The mRNA for this gene contains multiple polyadenylation sites, and is alternatively translated from non-AUG (CUG) and AUG initiation codons, resulting in five different isoforms with distinct properties. The CUG-initiated isoforms are localized in the nucleus and are responsible for the intracrine (meaning acting inside a cell)

effect, whereas, the AUG-initiated form is mostly cytosolic and is responsible for the paracrine (meaning secreted by a cell and locally acting on adjacent cells of a different type) and autocrine (meaning secreted by a cell and acting on cells of the same type) effects of this FGF.

The term "gene" as used herein refers to a region of DNA that controls a discrete hereditary characteristic, usually corresponding to a single protein or RNA. This definition includes the entire functional unit, encompassing coding DNA sequences, noncoding regulatory DNA sequences and introns.

The terms "good clinical outcome", "good outcome" or "GO" as used interchangeably herein refer to chemo-naïve relapse free/progression-free/disease free survival of greater than four (4) years.

The term "isolate" and its various grammatical forms as used herein refers to placing, setting apart, or obtaining a protein, molecule, substance, nucleic acid, peptide, cell or particle, in a form essentially free from contaminants or other materials with which it is commonly associated, separate from its natural environment.

The term "Kaplan Meier plot" or "Kaplan Meier survival curve" as used herein refers to the plot of probability of clinical study patients surviving in a given length of time while considering time in many small intervals. The Kaplan Meier plot assumes that: (i) at any time patients who are censored (i.e., lost) have the same survival prospects as patients who continue to be followed; (ii) the survival probabilities are the same for patients recruited early and late in the study; and (iii) the event (e.g., death) happens at the time specified. Probabilities of occurrence of event are computed at a certain point of time with successive probabilities multiplied by any earlier computed probabilities to get a final estimate. The survival probability at any particular time is calculated as the number of patients surviving divided by the number of patients at risk. Patients who have died, dropped out, or have been censored from the study are not counted as at risk.

The term "lymphocyte" refers to a small white blood cell formed in lymphatic tissue throughout the body and in normal adults making up about 22-28% of the total number of leukocytes in the circulating blood that plays a large role in defending the body against disease. Individual lymphocytes are specialized in that they are committed to respond to a limited set of structurally related antigens. This commitment, which exists before the first contact of the immune system with a given antigen, is expressed by the presence on the lymphocyte's surface membrane of receptors specific for determinants (epitopes) on the antigen. Each lymphocyte possesses a population of receptors, all of which have identical combining sites. One set, or clone, of lymphocytes differs from another clone in the structure of the combining region of its receptors and thus differs in the epitopes that it can recognize. Lymphocytes differ from each other not only in the specificity of their receptors, but also in their functions.

Two broad classes of lymphocytes are recognized: the B-lymphocytes (B-cells), which are precursors of antibody-secreting cells, and T-lymphocytes (T-cells).

B-Lymphocytes

B-lymphocytes are derived from hematopoietic cells of the bone marrow. A mature B-cell can be activated with an antigen that expresses epitopes that are recognized by its cell surface. The activation process may be direct, dependent on cross-linkage of membrane Ig molecules by the antigen (cross-linkage-dependent B-cell activation), or indirect, via interaction with a helper T-cell, in a process referred to as cognate help. In many physiological situations, receptor cross-linkage stimuli and cognate help synergize to yield more vigorous B-cell responses. (Paul, W. E., "Chapter 1: The immune system: an introduction," Fundamental Immunology, 4th Edition, Ed. Paul, W. E., Lippicott-Raven Publishers, Philadelphia (1999)).

T-Lymphocytes

T-lymphocytes derive from precursors in hematopoietic tissue, undergo differentiation in the thymus, and are then seeded to peripheral lymphoid tissue and to the recirculating pool of lymphocytes. T-lymphocytes or T cells mediate a wide range of immunologic functions. These include the capacity to help B cells develop into antibody-producing cells, the capacity to increase the microbicidal action of monocytes/macrophages, the inhibition of certain types of immune responses, direct killing of target cells, and mobilization of the inflammatory response. These effects depend on their expression of specific cell surface molecules and the secretion of cytokines. (Paul, W. E., "Chapter 1: The immune system: an introduction," Fundamental Immunology, 4th Edition, Ed. Paul, W. E., Lippicott-Raven Publishers, Philadelphia (1999)).

T cells differ from B cells in their mechanism of antigen recognition. Immunoglobulin, the B cell's receptor, binds to individual epitopes on soluble molecules or on particulate surfaces. B-cell receptors see epitopes expressed on the surface of native molecules. Antibody and B-cell receptors evolved to bind to and to protect against microorganisms in extracellular fluids. In contrast, T cells recognize antigens on the surface of other cells and mediate their functions by interacting with, and altering, the behavior of these antigen-presenting cells (APCs). There are three main types of antigen-presenting cells in peripheral lymphoid organs that can activate T cells: dendritic cells, macrophages and B cells.

T-cells are subdivided into two distinct classes based on the cell surface receptors they express. The majority of T cells express T cell receptors (TCR) consisting of $\alpha$ and $\beta$ chains. A small group of T cells express receptors made of $\gamma$ and $\delta$ chains. Among the $\alpha/\beta$ T cells are two sublineages: those that express the coreceptor molecule CD4 (CD4+ T cells); and those that express CD8 (CD8+ T cells). These cells differ in how they recognize antigen and in their effector and regulatory functions.

CD4+ T cells are the major regulatory cells of the immune system. Their regulatory function depends both on the expression of their cell-surface molecules, such as CD40 ligand whose expression is induced when the T cells are activated, and the wide array of cytokines they secrete when activated.

T cells also mediate important effector functions, some of which are determined by the patterns of cytokines they secrete. The cytokines can be directly toxic to target cells and can mobilize potent inflammatory mechanisms. In addition, T cells particularly CD8+ T cells, can develop into cytotoxic T-lymphocytes (CTLs) capable of efficiently lysing target cells that express antigens recognized by the CTLs. (Paul, W. E., "Chapter 1: The immune system: an introduction," Fundamental Immunology, 4th Edition, Ed. Paul, W. E., Lippicott-Raven Publishers, Philadelphia (1999)).

T cells can also be classified based on their function as helper T cells; T cells involved in inducing cellular immunity; suppressor T cells; and cytotoxic T cells.

Helper T Cells

Helper T cells are T cells that stimulate B cells to make antibody responses to proteins and other T cell-dependent antigens. TH2 cells are very effective in helping B-cells develop into antibody-producing cells, whereas TH1 cells are effective inducers of cellular immune responses, involving enhancement of microbicidal activity of monocytes and macrophages, and consequent increased efficiency in lysing microorganisms in intracellular vesicular compartments.

T Cells Involved in Inducing Cellular Immunity

T cells may act to enhance the capacity of monocytes and macrophages to destroy intracellular microorganisms. In particular, interferon-gamma (IFN-γ) produced by helper T cells enhances several mechanisms through which mononuclear phagocytes destroy intracellular bacteria and parasitism including the generation of nitric oxide and induction of tumor necrosis factor (TNF) production. The TH1 cells are effective in enhancing the microbicidal action because they produce IFN-γ. By contrast, two of the major cytokines produced by TH2 cells, IL-4 and IL-10, block these activities. (Paul, W. E., "Chapter 1: The immune system: an introduction," Fundamental Immunology, 4th Edition, Ed. Paul, W. E., Lippicott-Raven Publishers, Philadelphia (1999)).

Suppressor T Cells

A controlled balance between initiation and downregulation of the immune response is important to maintain immune homeostasis. Both apoptosis and T cell anergy (a tolerance mechanism in which the T cells are intrinsically functionally inactivated following an antigen encounter (Scwartz, R. H., "T cell anergy," Annu. Rev. Immunol., 21: 305-334 (2003)) are important mechanisms that contribute to the downregulation of the immune response. A third mechanism is provided by active suppression of activated T cells by suppressor or regulatory CD4+ T (Treg) cells. (Reviewed in Kronenberg, M. et al., "Regulation of immunity by self-reactive T cells," Nature 435: 598-604 (2005)). CD4+ Tregs that constitutively express the IL-2 receptor alpha (IL-2Rα) chain (CD4+ CD25+) are a naturally occurring T cell subset that are anergic and suppressive. (Taams, L. S. et 1., "Human anergic/suppressive CD4+CD25+ T cells: a highly differentiated and apoptosis-prone population," Eur. J. Immunol., 31: 1122-1131 (2001)). Depletion of CD4+CD25+ Tregs results in systemic autoimmune disease in mice. Furthermore, transfer of these Tregs prevents development of autoimmune disease. Human CD4+CD25+ Tregs, similar to their murine counterpart, are generated in the thymus and are characterized by the ability to suppress proliferation of responder T cells through a cell-cell contact-dependent mechanism, the inability to produce IL-2, and the anergic phenotype in vitro. Human CD4+CD25+ T cells can be split into suppressive (CD25high) and nonsuppressive (CD25low) cells, according to the level of CD25 expression. A member of the forkhead family of transcription factors, FOXP3, has been shown to be expressed in murine and human CD4+CD25+ Tregs and appears to be a master gene controlling CD4+CD25+ Treg development. (Battaglia, M. et al., "Rapamycin promotes expansion of functional CD4+ CD25+Foxp3+ regulator T cells of both healthy subjects and type 1 diabetic patients," J. Immunol., 177: 8338-8347 (200)).

Cytotoxic T Lymphocytes (CTL)

The CD8+ T cells that recognize peptides from proteins produced within the target cell have cytotoxic properties in that they lead to lysis of the target cells. The mechanism of CTL-induced lysis involves the production by the CTL of perforin, a molecule that can insert into the membrane of target cells and promote the lysis of that cell. Perforin-mediated lysis is enhanced by a series of enzymes produced by activated CTLs, referred to as granzymes. Many active CTLs also express large amounts of fas ligand on their surface. The interaction of fas ligand on the surface of CTL with fas on the surface of the target cell initiates apoptosis in the target cell, leading to the death of these cells. CTL-mediated lysis appears to be a major mechanism for the destruction of virally infected cells.

The terms "marker" or "cell surface marker" are used interchangeably herein to refer to an antigenic determinant or epitope found on the surface of a specific type of cell. Cell surface markers can facilitate the characterization of a cell type, its identification, and eventually its isolation. Cell sorting techniques are based on cellular biomarkers where a cell surface marker(s) may be used for either positive selection or negative selection, i.e., for inclusion or exclusion, from a cell population.

The terms "metastasis" or "metastases" as used herein refer to tumor growth or deposit that has spread via lymph or blood to an area of the body remote from the primary tumor.

The term "metastasize" as used herein refers to the spread of cancer from one part of the body to another. A tumor formed by cells that have spread is called a "metastatic tumor" or "metastasis." The plural form of "metastasis" is "metastases."

The terms "matrix metallopeptidase 9" or "MMP9" as used interchangeably herein refer to a member of the metalloproteinase (MMP) family involved in local proteolysis of the extracellular matrix and in leukocyte migration. MMP9 cleaves kispeptin (KiSS 1), a G-protein coupled receptor ligand of the G-protein coupled receptor GPR54, at a Gly-/-Leu bond, cleaves type IV and type V collagen, and degrades fibronectin.

The term "monocyte" as used herein refers to a type of immune cell that is made in the bone marrow and travels through the blood to tissues in the body where it becomes a macrophage. A monocyte is a type of white blood cell and a type of phagocyte.

The term "nucleic acid" as used herein refers to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

The term "nucleotide" as used herein refers to a chemical compound that consists of a heterocyclic base, a sugar, and one or more phosphate groups. In the most common nucleotides, the base is a derivative of purine or pyrimidine, and the sugar is the pentose deoxyribose or ribose. Nucleotides are the monomers of nucleic acids, with three or more bonding together in order to form a nucleic acid. Nucleotides are the structural units of RNA, DNA, and several cofactors, including, but not limited to, CoA, FAD, DMN, NAD, and NADP. Purines include adenine (A), and guanine (G); pyrimidines include cytosine (C), thymine (T), and uracil (U).

The term "peptide" is used herein to refer to two or more amino acids joined by a peptide bond.

The term "protein" is used herein to refer to a large complex molecule or polypeptide composed of amino acids. The sequence of the amino acids in the protein is determined by the sequence of the bases in the nucleic acid sequence that encodes it.

The terms "peptide", "polypeptide" and "protein" also apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein that protein is specifically reactive to antibodies elicited to the same protein but consisting entirely of naturally occurring amino acids. The terms "polypeptide", "peptide" and "protein" also are inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides may not be entirely linear. For instance, polypeptides may be branched as a result of ubiquitination, and they may be circular, with or without branching, generally as a result of posttranslational events, including natural processing event and events brought about by human manipulation which do not occur naturally. Circular, branched and branched circular polypeptides may be synthesized by non-translation natural process and by entirely synthetic methods, as well.

The terms "poor clinical outcome", "poor outcome" or "PO" are used interchangeably herein to refer to chemo-naïve primary refractory or early relapsing and chemo-exposed, multiple relapse within four (4) years or shortened survival/death two (2) to three (3) years after diagnosis.

The term "primer" refers to a nucleic acid which, when hybridized to a strand of DNA, is capable of initiating the synthesis of an extension product in the presence of a suitable polymerization agent. The primer is sufficiently long to uniquely hybridize to a specific region of the DNA strand. A primer also may be used on RNA, for example, to synthesize the first strand of cDNA.

The term "progression" as used herein refers to the course of a disease, such as HL, as it becomes worse or spreads in the body.

The term "progression free survival" or "PFS" as used herein refers to length of time during and after the treatment of a disease, such as cancer, that a patient lives with the disease but it does not get worse. In a clinical trial, measuring the progression free survival is one way to determine how well a new treatment works.

The term "quality of life" as used herein refers to the overall enjoyment of life, including aspects of an individual's sense of well-being and ability to carry out various activities.

The terms "recurrence" or "relapse" are used interchangeably herein to refer to the return of a cancer after a first-line treatment and after a period of time during which the cancer cannot be detected. The term "Hodgkin Lymphoma recurrence", "Hodgkin Lymphoma relapse", "recurrent Hodgkin Lymphoma", or "relapse Hodgkin Lymphoma" as used herein refers to the return of Hodgkin Lymphoma after treatment and after a period of time during which the Hodgkin Lymphoma cannot be detected. The term "early relapse" or "early recurrence" as used herein refers to a relapse or recurrence of cancer (e.g. Hodgkin's lymphoma) that occurs less than 1 year (<1 yr) after the end of therapy. The term "multiple relapse" or "multiple recurrence" as used herein refers to more than one relapse or recurrence of cancer (e.g. Hodgkin's lymphoma).

The term "refractory" as used herein refers to cancer that does not respond to treatment. The cancer may be resistant at the beginning of treatment or it may become resistant during treatment. The term "primary refractory" as used herein refers to the progression of disease (e.g., Hodgkin's lymphoma) during induction treatment or a partial or transient response (e.g. less than 60 days) to induction therapy. The term "induction therapy" as used herein refers to the first treatment given for a disease which is often part of a standard set of treatments, for example, surgery followed by chemotherapy and radiation. Induction therapy is often accepted as the best treatment option. Induction therapy is also known as "first-line therapy," "primary therapy" and "primary treatment."

The term "relapse-free survival (RFS)" as used herein refers to the length of time after primary treatment for a cancer during which the patient survives without any signs or symptoms of that cancer. Also called disease-free survival (DFS).

The term "relative" as used herein refers to something having, or standing in, some significant association to something else. The term "relative frequency" as used herein refers to the rate of occurrence of something having or standing in some significant association to the rate of occurrence of something else. For example, two cell types, X cells and Y cells occupy a given location. There are 5 X cells and 5 Y cells in that location. The relative frequency of cell type X is 5/10; the relative frequency of cell type Y is 5/10 in that location. Following processing, there are 5 X cells, but only 1 Y cell in that location. The relative frequency of cell type X following processing is 5/6, and the relative frequency of cell type Y following processing is 1/6 in that location.

The term "risk factor" as used herein refers to anything that raises the chances of a person developing a disease.

The terms "syndecan-1" or "SDC1" as used herein are used interchangeably to refer to a widely expressed transmembrane type I heparan sulfate proteoglycan that functions as an integral membrane protein and participates in cell proliferation, cell migration, and cell-matrix interactions.

The terms "subject" and "patient" are used interchangeably herein to refer to animal species of mammalian origin that may benefit from the administration of a drug composition or method of the described invention. Examples of subjects include humans, and other animals such as horses, pigs, cattle, dogs, cats, rabbits, mice, rats and aquatic mammals.

The term "syndrome" as used herein, refers to a pattern of symptoms indicative of some disease or condition.

According to one aspect, the described invention provides a method for predicting recurrence of Hodgkin Lymphoma (HL) in a subject treated with a first treatment regimen comprising: (a) providing a sample from the subject and a sample from a good clinical outcome control subject; (b) isolating total RNA comprising Fibroblast Growth Factor-2 (FGF2) and Syndecan-1 (SDC1) RNA from the sample from the subject and from the sample from the good clinical outcome control subject; (c) amplifying the total RNA from step (b); (d) measuring a level of expression of the FGF2 and the SDC1 RNA in the subject and in the good clinical outcome control subject; (e) comparing the level of expression of the FGF2 and the SDC1 RNA in step (d) expressed by the subject with the level of expression of the FGF2 and the SDC1 RNA in step (d) expressed by the good clinical outcome control subject, wherein an increased level of expression of the FGF2 RNA and the SDC1 RNA expressed by the subject compared to the level of expression of the FGF2 RNA and the SDC1 RNA expressed by the good clinical outcome control subject is indicative of recurrence of HL in the subject; (f) predicting recurrence of Hodgkin Lymphoma (HL) in the subject based on step (e); and (g) treating the subject with a second treatment regimen effective to treat the recurrence of HL.

According to one embodiment, the sample is selected from the group consisting of a tumor biopsy, blood, a lymph node and peripheral blood leukocytes (PBL).

According to one embodiment, amplifying is performed by Reverse Transcriptase-Polymerase Chain Reaction (RT-PCR).

According to one embodiment, the method for predicting recurrence of Hodgkin Lymphoma (HL) in a subject treated with a first treatment regimen further comprises: (d') measuring a level of expression of TGFβ1 and MMP9 RNA in the subject and in the good clinical outcome control subject; (e') comparing the level of expression of the TGFβ1 and the MMP9 RNA in step (d') expressed by the subject with the level of expression of the TGFβ1 and the MMP9 RNA in step (d') expressed by the good clinical outcome control subject, wherein an increased level of expression of the TGFβ1 RNA and the MMP9 RNA expressed by the subject compared to the level of expression of the TGFβ1 RNA and the MMP9 RNA expressed by the good clinical outcome control subject is indicative of recurrence of HL in the subject.

According to another aspect, the described invention provides a method for predicting poor clinical outcome in a Hodgkin Lymphoma (HL) subject comprising: (a) providing a sample from the HL subject and a sample from a good clinical outcome control subject; (b) isolating total RNA comprising Fibroblast Growth Factor-2 (FGF2) and Syndecan-1 (SDC1) RNA from the sample from the HL subject and from the sample from the good clinical outcome control subject; (c) amplifying the total RNA from step (b); (d) measuring a level of expression of the FGF2 and the SDC1 RNA in the HL subject and in the good clinical outcome control subject; (e) comparing the level of expression of the FGF2 and the SDC1 RNA in step (d) expressed by the HL subject with the level of expression of the FGF2 and the SDC1 RNA in step (d) expressed by the good clinical outcome control subject, wherein an increased level of expression of the FGF2 RNA and the SDC1 RNA expressed by the HL subject compared to the level of expression of the FGF2 RNA and the SDC1 RNA expressed by the good clinical outcome control subject is indicative of poor clinical outcome for the HL subject; (f) predicting poor clinical outcome for the HL subject based on step (e); and (g) replacing a treatment regimen likely to be ineffective with a treatment regimen effective to maintain the subject's quality of life.

According to one embodiment, the sample is selected from the group consisting of a tumor biopsy, blood, a lymph node and peripheral blood leukocytes (PBL).

According to one embodiment, amplifying is performed by Reverse Transcriptase-Polymerase Chain Reaction (RT-PCR).

According to one embodiment, the method for predicting poor clinical outcome in a Hodgkin Lymphoma (HL) subject further comprises: (d') measuring a level of expression of TGFβ1 and MMP9 RNA in the subject and in the good clinical outcome control subject; (e') comparing the level of expression of the TGFβ1 and the MMP9 RNA in step (d') expressed by the subject with the level of expression of the TGFβ1 and the MMP9 RNA in step (d') expressed by the good clinical outcome control subject, wherein an increased level of expression of the TGFβ1 RNA and the MMP9 RNA expressed by the subject compared to the level of expression of the TGFβ1 RNA and the MMP9 RNA expressed by the good clinical outcome control subject is indicative of poor clinical outcome in the HL subject.

According to another aspect, the described invention provides a method of detecting evidence of metastatic Hodgkin Lymphoma (HL) disease in a Hodgkin lymphoma subject comprising: (a) providing a peripheral blood leukocyte (PBL) sample from the HL subject and a PBL sample from a good clinical outcome control subject; (b) isolating total RNA comprising CD30, Fibroblast Growth Factor-2 (FGF2) and Syndecan-1 (SDC1) RNA from the PBL sample from the HL subject and from the PBL sample from the good clinical outcome control subject; (c) amplifying the total RNA from step (b); (d) measuring a level of expression of the CD30, the FGF2 and the SDC1 RNA in the HL subject and in the good clinical outcome control subject; (e) comparing the level of expression of the CD30, the FGF2 and the SDC1 RNA in step (d) expressed by the HL subject with the level of expression of the CD30, the FGF2 and the SDC1 RNA in step (d) expressed by the good clinical outcome control subject, wherein an increased level of expression of the CD30, the FGF2 and the SDC1 RNA expressed by the HL subject compared to the level of expression of the CD30, the FGF2 and the SDC1 RNA expressed by the good clinical outcome control subject is indicative of a metastasis in the HL subject; (f) detecting the evidence of metastasis in the HL subject based on step (e), and (g) implementing an appropriate treatment plan.

According to one embodiment, the amplifying is performed by Reverse Transcriptase-Polymerase Chain Reaction (RT-PCR).

According to one embodiment, the method of detecting evidence of metastatic Hodgkin lymphoma in a Hodgkin Lymphoma (HL) subject further comprises: (d') measuring a level of expression of CD15 RNA in the HL subject and in the good clinical outcome control subject; (e') comparing the level of expression of the CD15 RNA in step (d') expressed by the HL subject with the level of expression of the CD15 RNA in step (d') expressed by the good clinical outcome control subject, wherein an increased level of expression of the CD15 RNA expressed by the HL subject compared to the level of expression of the CD15 RNA expressed by the good clinical outcome control subject is indicative of a poor clinical outcome for the HL subject.

According to one embodiment, the method of detecting evidence of metastatic Hodgkin lymphoma in a Hodgkin Lymphoma (HL) subject further comprises: (d') measuring a level of expression of TGFβ1 and MMP9 RNA in the HL subject and in the good clinical outcome control subject; (e') comparing the level of expression of the TGFβ1 and the MMP9 RNA in step (d') expressed by the HL subject with the level of expression of the TGFβ1 and the MMP9 RNA in step (d') expressed by the good clinical outcome control subject, wherein an increased level of expression of the TGFβ1 RNA and the MMP9 RNA expressed by the HL subject compared to the level of expression of the TGFβ1 RNA and the MMP9 RNA expressed by the good clinical outcome control subject is indicative of metastatic HL in the HL subject.

According to one embodiment, the evidence of metastatic Hodgkin lymphoma in a Hodgkin Lymphoma subject comprises a circulating CD30+ cell with an FGF2+/SDC1+ immunophenotype. According to another embodiment, the circulating CD30+ cell with an FGF2+/SDC1+ immunophenotype is a circulating Hodgkin Lymphoma and Reed-Sternberg (HRS) cell.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials have been described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise.

The publications discussed herein are provided solely for their disclosure prior to the filing date of the present application and each is incorporated by reference in its entirety. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Materials and Methods
Bioinformatics

The BioXM software platform (Sophic Alliance, Rockville, Md.) was used to mine potential biomarkers for Hodgkin's lymphoma using the National Cancer Institute (NCI) Cancer Gene Index, which contains 7,000 cancer genes and 2,200 biomarker genes. These genes were annotated and validated from 18 million Medline abstracts and 24,000 Hugo genes from over 80 databases, using a combination of algorithmic methods (Biomax Informatics, Munich, Germany) that included natural language processing (NLP), Biomarker Role Codes, the NCI Cancer Thesaurus, and Karp's Evidence Codes (Karp P D et al., Pacif Sympo Biocomp; 2004: 190-201). The identification of potential biomarkers was performed by initiating queries on BioXM with a combination of search terms including Hodgkin's disease, lymphoma, cancer, biomarker, overexpression, up-regulation or down-regulation, and differentially-expressed. The bioinformatics-guided search generated 151 potential HL biomarkers (Table 5).

TABLE 5

HL-relevant genes identified by bioinformatics data mining

| | | | | | | | |
|---|---|---|---|---|---|---|---|
| ABCC2 (ATP-binding cassette, sub-family C (CFTR/MRP), member 2) | CCR4 (Chemokine (C-C motif) receptor 4) | CHEK2 (Checkpoint kinase 2) | ESR2 (Estrogen receptor 2 (ER beta)) | HSPA8 (Heat shock 70 kDa protein 8) | MALT1 (Mucosa associated lymphoid tissue lymphoma translocation gene 1) | OGG1 (8-oxo-guanine DNA glycosylase) | SPN (Sialophorin) |
| ABL1 (c-abl oncogene 1, non-receptor tyrosine kinase | CCR7 (Chemokine (C-C motif) receptor 7) | CLU (Clusterin) | EZH2 (Enhancer of zeste homolog 2) | HYAL2 (Hyaluronoglucosaminidase) | MLL (Myeloid/lymphoid or mixed-lineage leukemia) | PAX5 (Paired box 5) | SRC (v-src avian sarcoma (Schmidt-Ruppin A-2) viral oncogene homolog) |
| ADA (Adenosine deaminase) | CD14 (Cluster of differentiation 14) | CNR1 (Cannabinoid receptor 1) | FAS (TNF receptor superfamily member 6) | ICAM1 (Intercellular adhesion molecule 1) | MME (Membrane metalloendopeptidase) | PDCD1LG2 (Programmed cell death 1 ligand 2) | SST (Somatostatin) |
| ADIPOQ (Adiponectin, C1Q and collagen domain containing) | CD2 (Cluster of differentiation 2) | COL18A1 (Collagen, type XVIII, alpha 1) | FCER2 (Fc fragment of IgE, low affinity II, receptor for (CD23)) | ID2 (Inhibitor of DNA binding 2) | MPO (Myeloperoxidase) | PIK3CA (Phosphatidylinositol-4,5-bisphosphate 3-kinase, catalytic subunit alpha) | STAT6 (Signal transducer and activator of transcription 6, interleukin-4 induced) |

TABLE 5-continued

HL-relevant genes identified by bioinformatics data mining

| | | | | | | | |
|---|---|---|---|---|---|---|---|
| AR (Androgen receptor) | CD22 (Cluster of differentiation 22) | CP (Ceruloplasmin (ferroxidase)) | FCGR3A (Fc fragment of IgG, low affinity IIIa, receptor (CD16a)) | IFNG (Interferon gamma) | MS4A1 (Membrane-spanning 4-domains, subfamily A, member 1) | PIM1 (Pim-1 oncogene) | TBX21 (T-box 21) |
| ATF3 (Activating transcription factor 3) | CD27 (Cluster of differentiation 27) | CR2 (Complement component (3d/Epstein Barr virus) receptor 2) | FGF2 (Fibroblast Growth Factor 2) | IGHE (Immunoglobulin heavy constant epsilon) | MSH6 (mutS homolog 6) | PLK1 (Polo-like kiase 1) | TERF1 (Telomeric repeat binding factor (NIMA-interacting) 1) |
| B2M (Beta-2 microglobulin) | CD28 (Cluster of differentiation 28) | CSF3 (Colony stimulating factor 3 (granulocyte) | FHIT (Fragile histidine triad) | IGLα (Immunoglobulin lambda locus) | MUC16 (Mucin 16, cell surface associated) | POU2F2 (POU class 2 homeobox 2) | TFRC (Transferrin receptor) |
| B3GAT1 (Beta-1,3-glucuronyl transferase 1) | CD34 (Cluster of differentiation 34) | CTLA4 (Cytotoxic T-lymphocyte associated protein 4) | FLT3 (fms-related tyrosine kinase 3) | IL2 (Interleukin 2) | MYB (v-myb avian myelobastosis viral oncogene homolog) | PRL (Prolactin) | TGFB1 (Transforming growth factor, beta 1) |
| BCL10 (B-cell CLL/lymphoma 10) | CD38 (Cluster of differentiation 38) | CXCL10 (Chemokine (C-X-C motif) ligand 10) | FSCN1 (Fascin actin-bundling protein 1) | IL2RA (Interleukin 2 receptor, alpha) | MYC (v-myc avian myelocytomatosis viral oncogene homolog) | PTEN (Phosphatase and tensin homolog) | TIA1 (TIA1 cytotoxic granule-associated RNA binding protein) |
| BCL3 (B-cell CLL/lymphoma 3) | CD44 (Cluster of differentiation 44) | CXCR3 (Chemokine (C-X-C motif) receptor 3) | GATA3 (GATA binding protein 3) | IL3 (Interleukin 3) | MYOD1 (Myogenic differentiation 1) | PTH (Parathyroid hormone) | TNFRSF1β (Tumor necrosis factor receptor superfamily, member 1B) |
| BCL6 (B-cell CLL/lymphoma 6) | CD46 (Cluster of differentiation 46) | CXCR4 (Chemokine (C-X-C motif) receptor 4) | GFAP (Glial fibrillary acidic protein) | IRF4 (Interferon regulatory factor 4) | NAT2 (N-acetyltransferase 2 (arylamine N-acetyltransferase)) | REL (v-rel avian reticuloendotheliosis viral oncogene homolog) | TNFSF13β (Tumor necrosis factor (ligand) superfamily, member 13 B) |
| BIC (B-cell integration cluster) | CD5 (Cluster of differentiation 5) | CYP17A1 (Cytochrome P450, family 17, subfamily A, polypeptide 1) | GGT1 (Gamma-glutamyltransferase 1) | ITGA4 (Integrin, alpha 4 (antigen CD49D, alpha 4 subunit of VLA-4 receptor)) | NBN (Nibrin) | S100A6 (S100 calcium binding protein A6) | TP63 (Tumor protein p63) |
| BMI1 (BMI polycomb ring finger oncogene) | CD52 (Cluster of differentiation 52) | CYP3A43 (Cytochrome P450, family 3, subfamily A, polypeptide 43) | GHRL (Ghrelin/obestatin prepropeptide) | ITGAL (Integrin, alpha L (antigen CD11A (p180), lymphocyte function-associated antigen 1; | NF1 (Neurofibromin 1) | SDC1 (Syndecan 1) | TRAF1 (TNF receptor-associated factor 1) |

TABLE 5-continued

HL-relevant genes identified by bioinformatics data mining

| | | | | | | | |
|---|---|---|---|---|---|---|---|
| BSG (Basigin (OK blood group)) | CD55 (Cluster of differentiation 55) | D13S25 (Disrupted in B-cell neoplasia) | GPX1 (Glutathione peroxidase 1) | ITGB2 (Integrin, beta 2 (complement component 3 receptor 3 and 4 subunit)) | NME1 (NME/NM23 nucleoside diphosphate kinase 1) | SELL (Selectin L) | TRGα (T cell receptor gamma locus alpha) |
| CASP8 (Caspase 8, apoptosis-related cysteine peptidase) | CD59 (Cluster of differentiation 59) | DUT (Deoxyuridine triphosphatase) | HLA-A (Major histocompatibility complex, class I, A) | JUNB (jun B proto-oncogene) | NOS2 (Nitric oxide synthase 2, inducible) | SERPINE1 (Serpin peptidase inhibitor, clade E (nexin, plasminogen activator inhibitor type 1), member 1) | TSHB (Thyroid stimulating hormone, beta) |
| CCL17 (Chemokine (C-C motif) ligand 17) | CD70 (Cluster of differentiation 70) | E2F1 (E2F transcription factor 1) | HMGB1 (High mobility group box 1) | LDHA (Lactate dehydrogenase A) | NPM1 (Nucleophosmin (nucleolar phosphoprotein B23, numatrin)) | SERPING1 (Serpin peptidase inhibitor, clade G (C1 inhibitor), member 1) | VEGFA (Vascular endothelial growth factor A) |
| CCL5 (Chemokine (C-C motif) ligand 5) | CD79A (Cluster of differentiation 79A) | E2F3 (E2F transcription factor 3) | HP (Haptoglobin) | LEP (Leptin) | NPY (Neuropeptide Y) | SMARCB1 (SWI/SNF related, matrix associated, actin dependent regulator of chromatin, subfamily b, member 1) | WT1 (Wilms tumor 1) |
| CCND1 (Cyclin D1) | CDC25A (Cell division cycle 25A) | EDN1 (Endothelin 1) | HSPA1A (Heat shock 70 kDa protein 1A) | LEPR (Leptin receptor) | NRAS (Neuroblastoma RAS viral (v-ras) oncogene homolog | SOCS1 (Suppressor of cytokine signaling 1) | ZBTB16 (Zinc finger and BTB domain containing 16) |
| CCND3 (Cyclin D3) | CDK4 (Cyclin-dependent kinase 4) | ERBB2 (v-erb-b2 avian erythroblastic leukemia viral oncogene homolog 2) | HSPA4 (Heat shock 70 kDa protein 4) | MAL (mal, T-cell differentiation protein) | NTRK2 (Neurotrophic tyrosine kinase, receptor, type 2) | SPI1 (Spleen focus forming virus (SFFV) proviral integration oncogene) | |

Cell Lines and Cell Culture

The Hodgkin's lymphoma cell lines KM-H2 (established from a patient with HL of mixed cellularity), HD-MY-Z (established from pleural effusion of a patient with HL of nodular sclerosing type), HDLM-2 (established from a pleural effusion of a patient with HL of nodular-sclerosing type, stage IV), L-591 (an HL-derived Epstein-Ban virus (EBV)-positive cell line), and SUP-HD1 (established from a pleural effusion of a patient with HL of the nodular sclerosing type) were obtained from the German Collection of Microorganisms and Cell Cultures (Braunschweig, Germany). L-428 (established from a patient with HL of nodular sclerosing type), L-1236 (established from the peripheral blood of a patient with advanced HL), and L-540 (established from the bone marrow of a patient with HL of the nodular sclerosing type, stage IVB, preterminal stage) cells were generous gifts provided by Dr. Volker Diehl (University of Cologne, Germany). U-H01 (established from a patient with HL of nodular sclerosing type) and DEV (a cell line derived from a human medulloblastoma) cells were kind gifts from Dr. S. Brüderlein (University Hospital Ulm, Germany) and Dr. Debora De Jong (Netherlands), respectively. KM-H2, L-428, HD-MY-Z, and L-1236 cells were cultured in 90% RPMI 1640 supplemented with 10% fetal bovine serum (FBS). SUP-HD1 cells were grown in 80% McCoy's 5A medium containing 20% FBS. HDLM-2, L-540, and L-591 cells were grown in 80% RPMI 1640 supplemented with 20% FBS. U-H01 cells were grown in Iscove's MDM and RPMI 1640 (4:1) supplemented with 20% FBS. All culture media contained 2 mM L-glutamine, penicillin (100 U/ml), and streptomycin (0.1 mg/ml). Cultures were maintained at 37° C. with 5% CO2. The clinical characteristics of each cell line were previously documented and are presented in Table 4. DEV, KM-H2, and SUP-HD1 cells were derived from relapsing cases. HD-MY-Z, L1236, L428, and U-H01 cells were from refractory patients.

TABLE 6

Characteristics of HL Cell Lines*

| Cell Line | Clinical Characteristics | Anatomic Site of Primary Cell |
|---|---|---|
| DEV | relapse | Pleural fluid |
| HDLM2 | n/a | Pleural fluid |
| HD-MY-Z | refractory | Bone marrow |
| KM-H2 | relapse | Pleural fluid |
| L1236 | refractory/relapse | Peripheral blood |
| L428 | refractory | Pleural fluid |
| L540 | n/a | Bone marrow |
| L591 | n/a | Pleural fluid |
| SUP-HD1 | relapse | Pleural fluid |
| U-H01 | refractory | Pleural fluid |

*A review of the literature showed that all established HL cell lines were derived from primary malignant CD30+ cells isolated from extra-nodal sites: pleural fluid, bone marrow, and peripheral blood. No cell lines to date have been raised from primary HRS cells isolated from lymph nodes.

RNA Isolation and CDNA Systhesis

Total RNA from cell lines and peripheral blood (PBL) of HL patients was isolated using Trizol (Invitrogen, Carlsbad, Calif.). RNA from archived formalin fixed paraffin embedded (FFPE) tissue sections were extracted using RNeasy (Qiagen, Calif.) according to the manufacturer's instructions. Briefly, excess paraffin was trimmed off the sample block and 5-20 μm-thick sections were cut with a scalpel. Sections were immediately placed in a 2 ml microcentrifuge tube and the lid was closed. Next, 320 μl of Deparaffinization Solution was added to the microcentrifuge tube, the tube was vortexed for 10 seconds, followed by centrifugation to bring the sample to the bottom of the tube. The sample was incubated at 56° C. for 3 minutes, and then allowed to cool at room temperature. Next, 240 μl of Buffer PKD was added to the tube, the tube was vortexed and then centrifuged for 1 minute at 11,000×g at room temperature. Following centrifugation, 10 μl of proteinase K was added to the lower, clear phase and mixed by gentle pipetting. The sample containing proteinase K was incubated at 56° C. for 15 minutes, then at 80° C. for 15 minutes. After incubation at 80° C., the lower, uncolored phase was transferred into a new 2 ml microcentrifuge tube and incubated on ice for 3 minutes. Following incubation, the tube was centrifuged for 15 minutes at 20,000×g (13,500 rpm) and the supernatant was transferred to a new 2 ml microcentrifuge tube without disturbing the pellet. Next, DNAse Booster Buffer equivalent to a tenth of the total sample volume (approximately 25 μl) and 10 μl of DNAse I stock solution were added to the supernatant, mixed by inverting, and the tube was centrifuged to collect residual liquid from the sides of the tubes. The tube containing supernatant, DNAse Booster Buffer and DNAse I was incubated at room temperature for 15 minutes. Next, 500 μl Buffer RBC was added to the tube and mixed, followed by the addition of 1,200 μl of 100% ethanol. The sample was mixed by pipetting, followed by transferred of 700 μl of the sample to an RNeasy MinElute spin column placed in a 2 ml collection tube. The collection tube lid was closed and the the tube was centrifuged for 15 seconds at ≥8,000×g (≥10,000 rpm). Flow-through was discarded and the MinElute spin column step repeated until the entire sample was passed through the RNeasy MinElute spin column. Next, 500 μl of Buffer RPE was added to the MinElute spin column, the lid was closed, the collection tube was centrifuged for 15 seconds at ≥8,000×g (≥10,000 rpm), and the flow-through discarded. Again, 500 μl of Buffer RPE was added to the RNeasy MinElute spin column, the lid was closed, and the collection tube centrifuged for 15 seconds at ≥8,000×g (≥10,000 rpm) to wash the spin column membrane. The collection tube and flow-through were discarded after centrifugation. The RNeasy spin column was placed in a new 2 ml collection tube, the lid was open, the collection tube was centrifuged at full speed for 5 minutes, and the flow-through was discarded. Finally, the RNeasy MinElute spin column was placed in a new 1.5 ml collection tube, 30 μl of RNase-free water was added directly to the spin column membrane, the collection tube lid was closed and the tube was centrifuged for 1 minute to elute the RNA. The RNA concentration was spectrophotometrically determined at A260 (ThermoElectro Corporation). Total RNA integrity was checked by resolution on a 2% agarose gel under denaturing conditions. cDNA was generated using the SuperScript III RT First-Strand cDNA Synthesis Kit (Invitrogen, Carlsbad, Calif.) according to the manufacturer's protocol. Oligo-dT primers were used to generate cDNA from cell lines and peripheral blood lymphocyte (PBL)-derived RNA, and random hexamers were used for generating cDNA from RNA obtained from FFPE sections. Briefly, 5 μg of total RNA, 1 μl of primer (50 μM oligo(dT), or 50 ng/μl random hexamers) and 1 μl of Annealing Buffer were combined in a 0.2 ml thin-walled PCR tube on ice. The total volume in the PCR tube was adjusted to 8 μl by the addition of RNase/DNase-free water. The tube was incubated in a thermocycler at 65° C. for 5 minutes, immediately incubated on ice for 1 minute, then centrifuged to collect the contents of the tube. Next, 10 μl of 2× X First-Strand Reaction Mix and 2 μl of SuperScript III/RNaseOUT Enzyme Mix were added to the PCR tube on ice, the tube was vortexed and the contents of the tube collected by centrifugation. PCR tubes containing Oligo(dT) primers were incubated for 50 minutes at 50° C.; PCR tubes containing random hexamers were incubated 5-10 minutes at 25° C., followed by 50 minutes at 50° C. Next, PCR tubes were incubated at 85° C. for 5 minutes and immediately placed on ice. Finally, the cDNA synthesis reactions were stored at −20° C. or immediately used in a polymerase chain reaction (PCR).

Polymerase Chain Reaction (PCR)

Primer sets used for each gene were generated using online primer tools (University of Massachusetts; http://biotools.umassmed.edu/bioapps/primer3_www.cgi) (Table 7). Primers were designed to have lengths of 18 to 27 nucleotides (nt) with Tm=60° C. and 45 to 65% GC content, and were synthesized by a custom primer service provided by Invitrogen. Each primer pair was confirmed to generate a single discrete band by end-point PCR (BioRad DNA Engine Peltier Thermal Cycler) using cDNAs generated from normal spleen tissue. End-point PCR conditions consisted of denaturation at 95° C. for 30 seconds, annealing at 55° C. for 30 seconds, and primer extension at 72° C. for 1 minute. The primer pairs were designed to generate a PCR fragment of 150-170 base pairs (bp) for cell line- and peripheral blood lymphocyte (PBL)-derived cDNA, and 70-100 by for formalin-fixed, paraffin-embedded (FFPE)-derived cDNA (Table 5). The PCR products were resolved on a 2% agarose gel and visualized with ethidium bromide staining using a BioRad Imager. For qRT-PCR, each reaction consisted of 43 ng cDNA, 10 mmole primers and 10 μl 2× Power SYBR Green PCR Master Mix (Applied Biosystems, Foster City, Calif.) in a final volume of 20 μl, which was placed in a MicroAmp Fast Optical 96-Well Reaction Plate designed for use with the ABI7900 PCR system (Applied Biosystems). The reaction was performed using the standard mode (initial denaturation at 95° C. for 10 minutes followed by 40 cycles of 95° C. for 15 seconds and 60° C. for 1 minute). Each qRT-PCR reaction was done in triplicate, and each data set was analyzed with ABI7900 software. The amount of target mRNA was normalized to the expression levels of the housekeeping gene Glyceraldehyde 3-phosphate dehydrogenase (GAPDH). For cell lines, CD19 was used as control. For PBL analysis, the expression levels of CD14/63, CD38/19, and CD4/8 were compared against their expression in monocytes, CD19+ B cells, helper T cells, and cytotoxic T cells, respectively, of healthy donors (Miltenyi Biotech). Pooled normal cDNA (n=20) was used as a control for gene expression analysis of FFPE tissue-derived cDNA. The AACt method was used to calculate the fold-change relative to controls.

TABLE 7

Primer Sets for Each Gene Used in This Study

A. Primer Sets Used on PBL Samples

| Genes | Forward Sequence | Reverse Sequence |
|---|---|---|
| GAPDH | catggcctccaaggagtaag (SEQ ID NO: 1) | Aggggtctacatggcaactg (SEQ ID NO: 2) |
| CD4 | atgtggcagtgtctgctgag (SEQ ID NO: 3) | Cctagcccaatgaaaagcag (SEQ ID NO: 4) |
| CD8 | cagagctacccgcagagttc (SEQ ID NO: 5) | Ctccaaccctgacttgctgt (SEQ ID NO: 6) |
| CD30 | ccaacttagctgtcccctga (SEQ ID NO: 7) | Ctgggaccaatgctgttctc (SEQ ID NO: 8) |
| CD15 | gcaggtgggactttgttgtt (SEQ ID NO: 9) | Ccaaggacaatccagcactt (SEQ ID NO: 10) |
| CD19 | ttctgcctgtgttcccttg (SEQ ID NO: 11) | Cacgttcccgtactggttct (SEQ ID NO: 12) |
| CD38 | agatctgagccagtcgctgt (SEQ ID NO: 13) | aaaaaggcttccgtctctgg (SEQ ID NO: 14) |
| CD14 | gagctcagaggttcggaaga (SEQ ID NO: 15) | ttcggagaagttgcagacg (SEQ ID NO: 16) |
| CD63 | aaccacactgcttcgatcct (SEQ ID NO: 17) | aatcccacagcccacagtaa (SEQ ID NO: 18) |

TABLE 7 -continued

Primer Sets for Each Gene Used in This Study

| | | |
|---|---|---|
| FGF2 | tgctcagcagtcaccatagc (SEQ ID NO: 19) | cttgaggtggaagggtctcc (SEQ ID NO: 20) |
| SDC1 | cttcacactccccacacaga (SEQ ID NO: 21) | ggccactacagccgtattct (SEQ ID NO: 22) |

B. Primer Sets Used on FFPE Tissues

| Genes | Forward Sequence | Reverse Sequence |
|---|---|---|
| GAPDH | cctcaacgaccactttgtca (SEQ ID NO: 23) | ccctgttgctgtagccaaat (SEQ ID NO: 24) |
| TGFβ | gtacctgaacccgtgttgct (SEQ ID NO: 25) | cacgtgctgctccactttta (SEQ ID NO: 26) |
| MMP9 | ggcgctcatgtaccctatgt (SEQ ID NO: 27) | gccattcacgtcgtccttat (SEQ ID NO: 28) |
| CD30 | gaagctccacctgtgctacc (SEQ ID NO: 29) | ggtctggaatccacaagctc (SEQ ID NO: 30) |
| CD68 | tgacacccacggttacagag (SEQ ID NO: 31) | gtggttttgtggctcttggt (SEQ ID NO: 32) |
| SDC1 | taggacctttccaccacagc (SEQ ID NO: 33) | gaggctgcttcagtttggag (SEQ ID NO: 34) |
| FGF2 | tgaggctgagaggtcaaggt (SEQ ID NO: 35) | ctctgttgcctaggctggac (SEQ ID NO: 36) |

Selection of Clinical Samples

The selection criteria of peripheral blood samples were based on the response to first line therapy (Table 8). Twenty five nodular sclerosing-classical Hodgkin lymphoma (NS-cHL) patient samples registered in the database at the Hackensack University Medical Center were categorized into: 1) good outcome chemo-naïve, untreated, relapse-free/disease-free >4 years (n=12); 2) poor outcome chemo-naïve (untreated), primary refractory or early relapse (n=7); 3) chemo-exposed (pretreated), multiple relapses (n=6). Formalin-fixed, paraffin-embedded (FFPE), and fresh frozen (FF) lymph nodes from different HL stages and subtypes were obtained from Thomas Jefferson University, the Tissue Repository of the Hackensack University Medical Center, and Proteogenex (Culver City, Calif.). Biospecimens with the relevant clinical characteristics were grouped into good outcome (GO, relapse free/disease free >4 years, n=20) and poor outcome (PO, shortened survival-death 2 to 3 years after diagnosis). A lymphoma tissue array was obtained from US Biomax (Rockville, Md.).

TABLE 8

Patient Characteristics for Each Clinical Outcome Group

| | Donors | Sex | Clinical Diagnosis | | | | |
|---|---|---|---|---|---|---|---|
| | | | Subtype | Bulky (B)/non-bulky (NB) | Age | Stage at diagnosis | Treatment | Outcome |
| Good Outcome | GO1 | F | NS | UNSP | 29 | IV | ABVD | PFS |
| | GO2 | F | NS | B | 41 | IIA | Stanford V + Rad | PFS |
| | GO3 | F | NS | NB | 79 | IA | ABVD + Rad | PFS |
| | GO4 | F | NS | B | 22 | IIA | Stanford V + Rad | PFS |
| | GO5 | M | NS | NB | 43 | IIA | ABVD | PFS |
| | GO6 | M | NS | B | 20 | IIA | ABVD + R | PFS |
| | GO7 | F | NS | NB | 64 | IIA | ABVD | PFS |
| | GO8 | F | NS | B | 51 | IIIB | ABVD + Rad | PFS |
| | GO9 | F | NS | UNSP | 54 | IV | ABVD | PFS |

TABLE 8-continued

Patient Characteristics for Each Clinical Outcome Group

| | Donors | Sex | Subtype | Clinical Diagnosis Bulky (B)/non-bulky (NB) | Age | Stage at diagnosis | Treatment | Outcome |
|---|---|---|---|---|---|---|---|---|
| | GO10 | F | NS | UNSP | 22 | IIA | ABVD | PFS |
| | GO11 | F | NS | NB | 25 | IIA | ABVD | PFS |
| | GO12 | F | NS | NB | 26 | IIB | ABVD | PFS |
| Poor Outcome (CN) | PO1 | M | NS | UNSP | 48 | IIA | ABVD + R (1); R + Bendamustine (2); Zevalin (3) | Rel. |
| | PO2 | M | NS | B | 24 | II | ABVD (1); acc. BEACOPP (4X) std BEACOPP (2X)(2); Bendamustine + R (3); IGEV + Rad (4); BCPAT (5); CR PT | Ref. |
| | PO3 | M | NS | UNSP | 25 | IIB | ABVD (1); ICE X 3 followed by BPCAT + Local Rad (2); CR PT | Rel. |
| | PO4 | F | NS | B | 25 | IIA | ABVD (1); ICE (2X) (2); GVD + R + Rad (3); HCVAD 1A (4); F + ECPOCH TH2 Allogenic (5); CR PT | Ref. |
| | PO5 | M | NS | B | 49 | IV | ABVD + R (1); ICE + R followed by BCPAT (2); R for EBV reactivation (3); CR PT | Ref. |
| | PO6 | M | NS | NB | 20 | IIIB | ABVD + R (1); ICE x 2 (2); IGEV + R x 2 (3); Rad (4); BCPAT (5); CR | Ref. |
| Poor Outcome (CE) | PO1 | M | NS | UNSP | 31 | IIIB | ABVD (1); ABVD (2); CPPV (3); DICE followed by BPCAT (4); HCVAD 1A + 1B (5); FMPAL (5) | Rel. |
| | PO2 | F | NS | UNSP | 23 | II | MOPP + ABVD (1); BEAC conditioning pre auto transplant (2); Rad (3); ICE X 2/ESHAP X 6 (4) | Rel. |
| | PO3 | M | NS | UNSP | 21 | II | ABVD (1); ESHAP x 1 followed by BCPAT (2); Gemcitabine + Navelbine (3); HCVAD X 3A's followed by FMPAL (4); DLI infusion (5); | Rel. |

TABLE 8-continued

Patient Characteristics for Each Clinical Outcome Group

Clinical Diagnosis

| Donors | Sex | Subtype | Bulky (B)/non-bulky (NB) | Age | Stage at diagnosis | Treatment | Outcome |
|---|---|---|---|---|---|---|---|
| PO4 | F | NS | B | 20 | IIA | Revlamid + DLI infusion (6) ABVD + Rad (1); ICE + auto transplant (2); bone resection + Rad (3); WU protocol phase II Revlamid (4); TH2 Study (EPOCH + FR) NCI protocol followed by BEACOPP pre transplant (5); (No rel.) | Rel. |
| PO5 | M | NS | UNSP | 30 | IIB | ABVD + Rad (1); ICE + Gemzar followed by BPCAT (2); ESHAP X 3 (3); HCVAD X 5 followed by FMPAL (4); Bendamustine (SK Protocol) 08-041 (5) | Rel. |
| PO6 | M | NS | UNSP | 49 | IIIB | ABVD (1); ICE followed by BCPAT; GVD + R (3); Revlamid (4) SGN-40 x 2 cycles (5); (PD) | Rel. |
| PO7 | M | NS | UNSP | 21 | IIA | ABVD (1); ESAHP (2); IGEV (3); BEAC + Rad (4); GDP; R + MOPP (5); died of PD | Rel. |

ABVD: Adriamycin, Bleomycin, Vinblastine, Dacarbazine;
acc: accelerated;
BCPAT: BEAM conditioning pre-auto transplant;
CR: Complete Remission;
CE: Chemo-exposed;
CN: Chemo-naïve;
BEACOPP: Bleomycin, Etoposide, Adriamycin, Cyclophosphamide, Vincristine, Procarbazine, Prednisone;
CPPV: Chlorambucil, Procarbazine, Prednisone, Vinblastine;
DICE: Deamethasone, Ifosfamide, Cisplatin, Etoposide;
EPOCH: Etoposide, Vincristine and Doxorubicin with bolus Cyclophosphamide;
ESHAP: Etoposide, Methylprednisolone, Ara-C and Cisplatin;
FMPAL: Fludarabine, Melphalan, Pre-allo transplant;
GVD: Gemcitabine, Vinorelbine, liposomal Vincristine;
HCVAD: Hyper Cyclophosphamide, Vincristine, Adriamycin and Dexamethasone;
ICE: Ifosfamide, Carboplatin, Etoposide;
IGEV: Ifosfamide, Gemcitabine and Vinorelbine;
PFS: Progression Free Survival;
PT: Post transplant;
Rel: Relapse;
Ref: Refractory;
R: Rituximab;
Rad: Radiation;
SK: Sloane Kettering;
Std: Standard;
WU: Washington University Immunohistochemistry Formalin-fixed, paraffin-embedded (FFPE) and fresh frozen lymph nodes from different stages and subtypes of HL were purchased from US Biomax and Proteogenex. FFPE sections (5 µm) mounted on slides were dewaxed twice with Histochoice clearing agent (Amresco, Solon, Ohio) for 10 minutes each, then sequentially hydrated in 100%, 90%, 80%, 70%, and 50% ethanol followed by equilibration in PBS for 5 minutes each. All antigen retrievals were carried out in a 95° C. water bath for 20-30 minutes (depending on the antigen) using high pH (pH 9) buffer (DAKO) for FGF2, SDC1, MMP9, and CD68, or low pH (pH 6) buffer (DAKO) for CD30, TGFβ1, and CD20. The sections were cooled for 20 minutes at room temperature and then washed twice with PBS for 5 minutes. Endogenous peroxidases were quenched by incubating the sections in 3% $H_2O_2$ solution in PBS for 10 minutes followed by rapid washes in PBS at room temperature. A hydrophobic PAP pen (Vector Labs, Burlingame, Calif.) was used to make a dam around the sections, which were then blocked at room temperature for 2 hours with 1% BSA containing 5% swine serum in PBS, followed by overnight incubation with primary antibodies at 4° C. Monoclonal antibodies for CD30 (clone Ber-H2, DAKO), SDC1 (clone BB4, Abd Serotec), CD68 (clone PG-M1, DAKO), and CD20 (clone L26, DAKO) were used at dilutions of 1:20, 1:40, 1:50, and 1:100, respectively. Rabbit polyclonal antibodies for FGF2 (Santa Cruz), TGFβ1 (Santa Cruz), and MMP9 (DAKO) were used at dilutions of 1:200, 1:200, and 1:100, respectively. Stained sections were washed three times in PBS/0.1% Tween-20 for 5 minutes each and then once in PBS for 5 minutes. Signal detection was carried out using a labelled streptavidin-Biotin (LSAB) kit according to the manufacturer's instructions (DAKO), with minor modifications. Briefly, sections were incubated in Biotin-labelled affinity isolated goat anti-rabbit and goat anti-mouse immunoglobulin in PGS containing stabilizing protein and 0.15 mol/L sodium azide (Biotinylated Link Antibody) for 30 minutes at room temperature and washed three times in 0.1% PBS containing stabilizing protein and antimicrobial agents for 5 minutes each. Sections were then incubated in streptavidin-HRP for 30 minutes and washed as described above. Signals were visualized by incubating the slides in a solution of 1 ml substrate buffer with 1 drop chromogen, and immediately rinsed in tap water. The sections were counterstained with hematoxylin (Vector Labs) for 22 seconds and immediately washed in tap water before mounting with Aqua Mount (Vector Labs). Photomicrographs of stained tissues were generated with an Axio Cam MRc camera coupled to an Axio Imager Microscope (Carl Zeiss, Thornwood, N.Y.). Positive control slides included tonsil for CD20, CD68, and SDC1, and ALCL for CD30 (on lymphoma array). For qualitative scoring, no staining was assigned a score of 0, weak staining 1, moderate staining 2, and intense staining, 3.

Immunofluorescence

Double immunofluorescence analysis was performed on 5 µm formalin-fixed, paraffin-embedded (FFPE) and optimal cutting temperature medium (OCT)-embedded 8 µm fresh frozen (FF) tissue sections that were mounted on positively-charged frosted slides (Histoserv, Germantown, Md.). FFPE sections were processed similarly to the preparation used for IHC. OCT-embedded FF sections were thawed at room temperature for 20 minutes, rinsed briefly in PBS, and then fixed in 3.7% formaldehyde (Electron Microscopy Sciences, Pa.) for 20 minutes at room temperature. The remaining steps for immunofluorescence signal detection were carried out using a Tyramide Signal Amplification (TSA) Detection system (Invitrogen), an enzyme-mediated detection method that uses horseradish peroxidase (HRP) to generate high-density labeling of a target protein or nucleic acid in situ, according to the manufacturer's instructions. Briefly, tyramide stock solution was prepared by dissolving the solid material provided (Component A) in 150 µL of DMSO (Component B) and inverting the vial several times to dissolve any tyramide coating the sides of the vial. A 1% (10 mg/mL) solution of blocking reagent (BSA) was prepared in PBS. The HRP conjugate stock solution was prepared by reconstituting the material provided in 200 µL of PBS. Amplification buffer/0.0015% $H_2O_2$ was prepared by adding 30% hydrogen peroxide (Component F) to amplification buffer (Component E) to obtain a final concentration of 0.0015% $H_2O_2$. Cells or tissue were rinsed with PBS that has been warmed to 37° C. and fixed with 3.7% formaldehyde, or paraformaldehyde, in PBS at room temperature for 20 minutes. Next the cells or tissue were rinsed with PBS, permeabilized with 0.1-0.2% Triton® X-100 solution for 5-10 minutes at room temperature, or with acetone at ≤−20° C. for 10 minutes and rinsed again with PBS. Following rinsing with PBS, the cells or tissue were incubated with 1% blocking reagent for 60 minutes at room temperature or 37° C. The cells or tissue were labeled with primary antibody diluted in 1% blocking reagent for 60 minutes at room temperature and rinsed three times with PBS. Next, a working solution of the HRP conjugate was prepared by diluting the stock solution 1:100 in 1% blocking solution and 100 µL of the HRP conjugate working solution was applied to the cells or tissue and incubated for 30-60 minutes at room temperature. The cells or tissue were rinsed three times with PBS. Next, a tyramide working solution was prepared by diluting the tyramide stock solution 1:100 in amplification buffer/0.0015% $H_2O_2$ just prior to labeling and 100 µL of the tyramide working solution was applied to the cells or tissue and incubated for 5-10 minutes at room temperature. The cells or tissue were rinsed three times with PBS. The cells or tissue were mounted and examined by fluorescence microscopy. Monoclonal and polyclonal signals were detected with Alexa Fluor 488 and Alexa Fluor 546, high-performance Alexa Fluor® dyes, respectively. The antibodies used were the same as for immunohistochemistry, except that an SDC1 rabbit polyclonal antibody (Sigma-Aldrich) was used for CD30-SDC1 double staining. Slides were counterstained with Hoechst 33342, visualized with a Leica DMI 6000B inverted microscope, and analyzed using Leica MM AF software, version 1.5 (Leica Microsystems). Slides were independently reviewed and verified by two pathologists.

Statistics

Data analyses were performed using SAS 9.1.3, StatView 5, or JMP 4. Contingency and likelihood ratio analyses were used to determine the independence of staging and prognosis. The mean fold-change for each sample was determined from triplicates of the qRT-PCR data. Analysis of variance (ANOVA) and F statistics were used to determine differences between the means of the poor outcome group and other outcome groups. Fisher's protected least significant difference (PLSD) was used to determine pair-wise significant differences between group means.

Example 1

Characteristics of Clinical Samples

The characteristics of clinical samples for PBL are listed in Table 8. Retrospective clinical samples of PBL collected from 25 NS-cHL patients (average age: 34.48 years, range: 20-79, 13 females and 12 males) were categorized into three groups on the basis of their response to first line therapy: (1) good outcome pre-therapy: chemo-naïve relapse free/progression-free survival >4 years (GO, n=12); (2) poor outcome pre-therapy: chemo-naïve primary refractory or early relapsing (PO(CN), n=6); and (3) poor outcome post-therapy: chemo-exposed, multiple relapse within 4 years (PO(CE), n=7). Among the pre-therapy, chemo-naïve patients (n=18), 68% were diagnosed during early disease stages (I and II), 10% (n=2) at stage III, and 15% (n=3) at stage IV. Of the early stage diagnoses (I and II, n=13), more than 30% (n=4) were either primary refractory or developed early relapses shortly after frontline therapy. The remaining PO(CN) samples were from advanced stages (III & IV). Also, 56% (n=14) of the patients were younger than the average age (34.48 years) at diagnosis.

Example 2

Bioinformatics and Data Mining for Potential Biomarkers

To enhance the specificity of potential poor outcome biomarkers, a bioinformatics based approach was used. Bioinformatics-guided approaches have the unique advantage of avoiding challenges that arise from the cost, time, and labor that are required to identify potential biomarkers for human diseases.

Potential biomarkers for HL were selected from the Cancer Gene Index and screened using a library of HL cell lines. The BioXM software platform (Sophic Alliance, Rockville, Md.) was used to mine published data for more than 7,000 cancer genes and 2,200 biomarker genes. These genes were annotated and validated from 18 million Medline abstracts and 24,000 HUGO genes using a combination of algorithmic methods (Biomax Informatics, Munich, Germany), including natural language processing (NPL), Biomarker Role Codes, the NCI Cancer Thesaurus, and Karp's Evidence Codes (Karp P D et al., Pacif Sympo Biocomp; 2004: 190-201). Compilation of the outputs resulted in the identification of 151 candidate HL biomarker genes (Table 5).

Example 3

Clinical Outcome of HL Patients is Not Associated with Tumor Staging, Age, Bulkiness or First-Line Therapy In this study, contingency analyses was performed on 25 NS-cHL patients in order to determine whether an association exists between clinical outcome and tumor staging, patient age, bulky disease or first-line therapy. The results of this study are shown in FIG. 1. Contingency analyses of 25 NS-cHL patients did not identify associations between clinical outcomes (good outcome (GO), n=12, vs. poor outcome (PO), n=13) and major clinical characteristics such as clinical stage (p>0.4), age group (p>0.11), bulky disease (with or without inclusion of unspecified data, p>0.18), and frontline therapy (p>0.27) (FIG. 1, Table 8). The same analysis of the dataset with the PO (CE) group excluded also failed to identify any relationship between outcome and clinical phenotype. This result differs from established trends used in stratification schemes of current prognostic scoring systems. Without being bound by theory, these results suggest that there may be undetermined molecular pathways that are altered in subsets of NS-cHL patients who are predisposed to primary refractory disease or experience multiple relapses shortly after first-line treatments, i.e., alteration of specific molecular signaling may contribute to clinical outcome.

Example 4

FGF2 and SDC1 are Overexpressed by HL Cell Lines

In this study, ten HL cell lines were used to identify bioinformatics-identified genes overexpressed by Hodgkin lymphoma cells. Established HL cell lines represent poor outcome HL because they were generated from primary Hodgkin's and Reed-Sternberg (HRS) cells isolated from extranodal sites of pleural effusion, bone marrow, or peripheral blood. Extranodal HL implies lymphatic and hematogenous dissemination via circulation.

Figure 2:
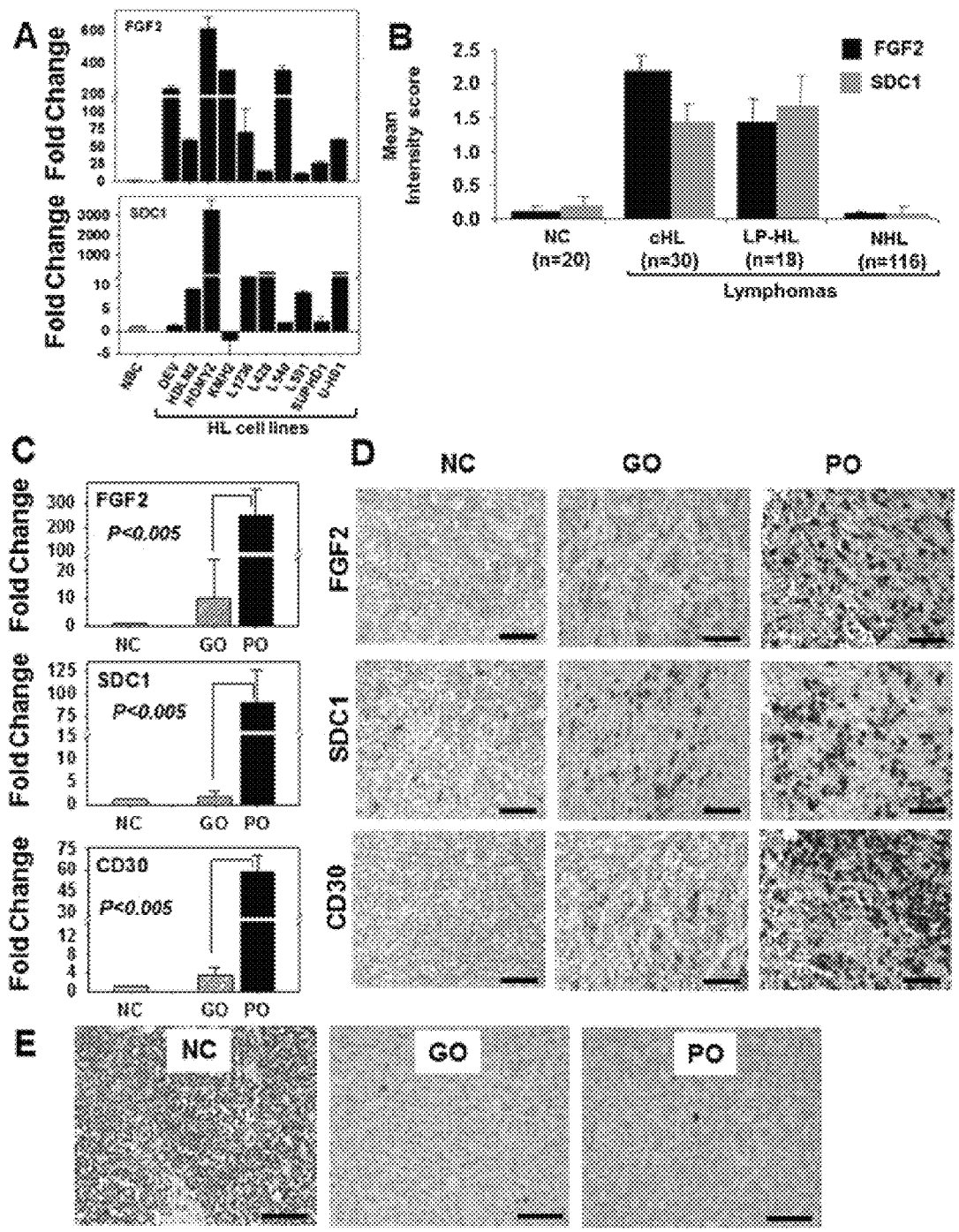
FIG. 2 shows that FGF2 and SDC1 are overexpressed by HL cell lines and by CD30+ cells in the poor outcome HL patient group. (A) FGF2 and SDC1 expression in 10 different HL cell lines (solid black bar) is represented as the normalized fold change relative to purified normal B-cells (NBC, solid gray bar). The standard error (SE) for each cell line is indicated above each bar. (B) Qualitative mean intensity scores for FGF2 (solid black bar) and SDC1 (solid gray bar) from immunostained tissues in an array format consisting of 10 normal, 30 classical HL (cHL), and 18 Lymphocyte Predominant-HL (LP-HL) and 116 Non-HL (NHL) samples (y-axis). Immunostaining intensity was scored as 0 (no staining), 1 (weak), 2 (moderate), or 3 (intense). Standard error bars of the mean are indicated. (C) FGF2, SDC1, and CD30 mRNA expression levels in normal lymph node controls (NC, solid gray bar) and HL tissues associated with good outcome (GO, striped bar) and poor outcome (PO, solid black bar) were analyzed by qRT-PCR. The measurements represent the fold change after normalization with the NC group. (D) The same set of normal and HL tissues from (B) were immunostained for FGF2, SDC1, and CD30. Representative normal and stage II GO and PO patients are shown. (E) CD20 expression in normal lymph nodes and HL tissues analyzed by immunostaining. The significance of all qRT-PCR data comparing GO and PO is indicated (p<0.005). Scale bars represent 100 µm.

RNA was isolated from the ten HL cell lines listed in Table 6 and screened using qRT-PCR for altered expression of a set of bioinformatics-identified genes representing multiple signaling pathways such as apoptosis, proliferation, angiogenesis, and metastasis (Table 5). The results of this study are depicted in FIG. 2. Expression screening data for these genes showed a consistent and robust overexpression of FGF2 and SDC1 in eight of ten HL cell lines that were originally derived from primary HRS, compared to their expression by primary B cells (FIG. 2A).

Example 5

FGF2 and SDC1 are Overexpressed by CD30+ Cells in Poor Outcome (PO) HL Patients

In this study, immunohistochemistry and qRT-PCR were employed to determine whether FGF2 and SDC1 genes are overexpressed by CD30+ cells in poor outcome (PO) HL patients. CD30 and CD15 are markers known to be expressed on classical Hodgkin Lymphoma Reed-Sternberg (HRS) cells.

To determine whether FGF2 and SDC1 are overexpressed specifically in HL patient samples, 48 HL and 116 major subtypes of non-Hodgkin lymphoma (NHL) tissue sections in a tissue microarray format were analyzed by immunohistochemical methods. Qualitative scoring of immunostaining showed that FGF2 and SDC1 were predominantly overexpressed in HL compared to NHL or normal lymph nodes ($p<0.05$) (FIG. 2B).

In addition, 67 archived HL samples with clinical outcome data were analyzed by qRT-PCR and immunohistochemical methods in order to determine the gene expression profile of FGF2 and SDC1 in HL tissues. FIG. 2 shows the results of this study. The PCR data showed that, when compared to normal lymph node controls, all HL tissues overexpressed FGF2 and SDC1. Tissues from poor outcome patients (n=9) showed 246- and 91-fold increases in FGF2 and SDC1 levels, respectively, while tissues from good outcome patients (n=20) had only 10- and 2-fold respective increases. Thus, the poor outcome group expressed 24-fold more FGF2 and 56-fold more SDC1 than the good outcome group (FIG. 2C). Expression of CD30 was increased by 59-fold in the poor outcome group and 3-fold in the good outcome group. Without being bound by theory, these data suggest that the fold-difference between the poor and good outcome groups is largely contributed by CD30 positive (CD30+) cells in the poor outcome group. Immunostaining of FGF2 and SDC1 was intense in the poor outcome group but weak to moderate in the good outcome group (FIG. 2D). In HL tissues from the poor outcome group, CD30+FGF2+SDC1+ cells were seen in clusters in whole mount HL tissues (data not shown). Immunostaining of the same tissues indicated that CD20 (B-lymphocyte antigen) expression was significantly reduced in all HL tissues compared to normal controls (FIG. 2E). Without being bound by theory, these data suggest that the increase in staining and gene expression of FGF2 and SDC1 in the poor outcome group is a consequence of increased numbers of CD30+ cells rather than of CD20+ B-cells.

Example 6

CD30+ Cells Coexpress FGF2 and SDC1 in Macrophage-Rich Tissues from the Poor Outcome (PO) Group of HL Patients In this study, double immunofluorescence analysis was performed on FFPE and OCT-embedded fresh frozen macrophage-rich tissues from different stages and subtypes of HL in order to determine whether FGF2 and SDC1 genes are overexpressed by CD30+ cells in poor outcome (PO) HL patients. CD30 and CD15 are markers known to be expressed on classical Hodgkin Lymphoma Reed-Sternberg (HRS) cells.

Figure 3:
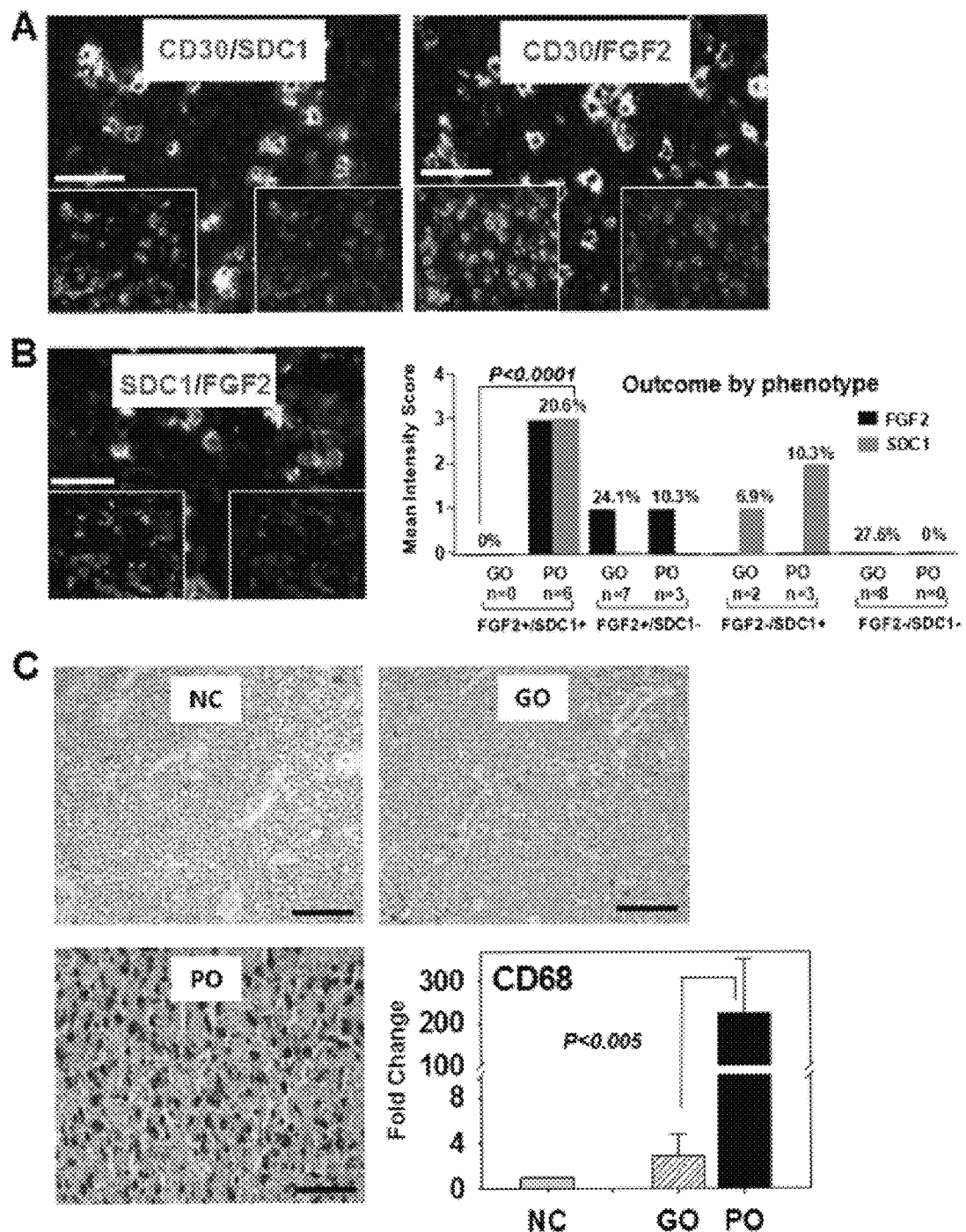
FIG. 3 shows that CD30+ cells coexpress FGF2 and SDC1 in macrophage-rich HL tissues with poor outcome. (A) Double immunofluorescent staining showing expression of either FGF2 or SDC1 by CD30+ cells of poor outcome samples. Individual green or red fluorescence is depicted at the bottom of each image; scale bar (white solid bar) represents 100 µm. (B) Distribution of the immunophenotypes by outcome. The mean intensity scores for FGF2 (solid gray bar) and SDC1 (solid black bar) (y-axis) for the good outcome (GO) and poor outcome (PO) groups of HL patients. Immunofluorescence intensity was scored as 0 (no staining), 1 (weak), 2 (moderate), or 3 (strong) for FGF2+ or FGF2− and SDC1+ or SDC1−. The frequency (%) of expression of each combination of FGF2+/− and SDC1+/− among all tissue sections is indicated above each bar. (C) CD68 macrophage marker expression was analyzed by immunostaining (image) and qRT-PCR (graph) in normal lymph node control (NC), good outcome (GO), and poor outcome (PO) groups of HL patients. The fold-change in CD68 mRNA was calculated after normalization with NC. Significance of all qRT-PCR data comparing GO and PO is indicated for (B) and (C) (p<0.005). Scale bars represent 100 μm.

Double immunofluorescence analysis of HL tissues showed that all sections from the poor outcome group had clusters of CD30+ cells that coexpressed FGF2 or SDC1 (FIG. 3A). The majority of tissues showed weak or no FGF2 or SDC1 staining or weak staining for both FGF2 and SDC1 (FIG. 3B graph). All FGF2+/SDC1+ cells with intense fluorescence (n=6) were associated with the poor outcome group, and often clustered in several regions within the whole mount HL tissues. Clusters of FGF2−/SDC1+ and FGF2+/SDC1− cells were seen in each of the remaining poor outcome HL tissues (n=3). Also, clusters of FGF2+/SDC1− or FGF−/SDC 1− cells were seen in good outcome HL tissues (FIG. 3B-graph). These results suggest that FGF2 and SDC1 coexpression in CD30+ cells or in clusters of cells may trigger molecular signaling that contributes to a poor clinical outcome. A Kaplan-Meier analysis also indicated that the FGF2+/SDC1+ immunophenotype of CD30+ cells is associated with shortened survival (not shown).

CD68+ tumor-associated macrophages were recently shown to be associated with adverse outcomes, including shortened survival (Steidl C et al., N Engl J Med 2010, 362(10): 875-885), which is a consequence of primary refractory and early relapsing cHL. Therefore, we evaluated the number of CD68+ tumor-associated macrophages in the good and poor outcome groups. More CD68+ tumor-associated macrophages were present in the PO group than in either the GO group or among normal controls (FIG. 3C). CD68 immunostaining was also more intense in the PO group than in the other groups (FIG. 3C). The analysis of CD68+ tumor-associated macrophages and IHC staining data were verified by qRT-PCR, which demonstrated that CD68 expression in the poor outcome group was 77-fold greater than in the good outcome group, and 224-fold greater than in normal lymph nodes (FIG. 3C, graph). Without being bound by theory, these results suggest that a large tumor macrophage population promotes poor clinical outcome by potentiating aggressive CD30+ tumor cells in a subset of HL patients, and some of these CD30+ cells express FGF2 and SDC1.

Example 7

Metastatic Markers TGFβ1 and MMP9 are Overexpressed in the Poor Outcome (PO) Group of HL Patients and by HL Cell Lines Poor prognosis in HL typically correlates with the presence of tumor cells in extranodal sites distant from the primary tumor. To investigate the metastatic potential of HL tissues having an abundance of CD30+/FGF2+/SDC1+ cells and poor clinical outcome, tissue sections were immunostained for the expression of metastatic markers TGFβ1 and MMP9 (FIG. 4A).

Figure 4:
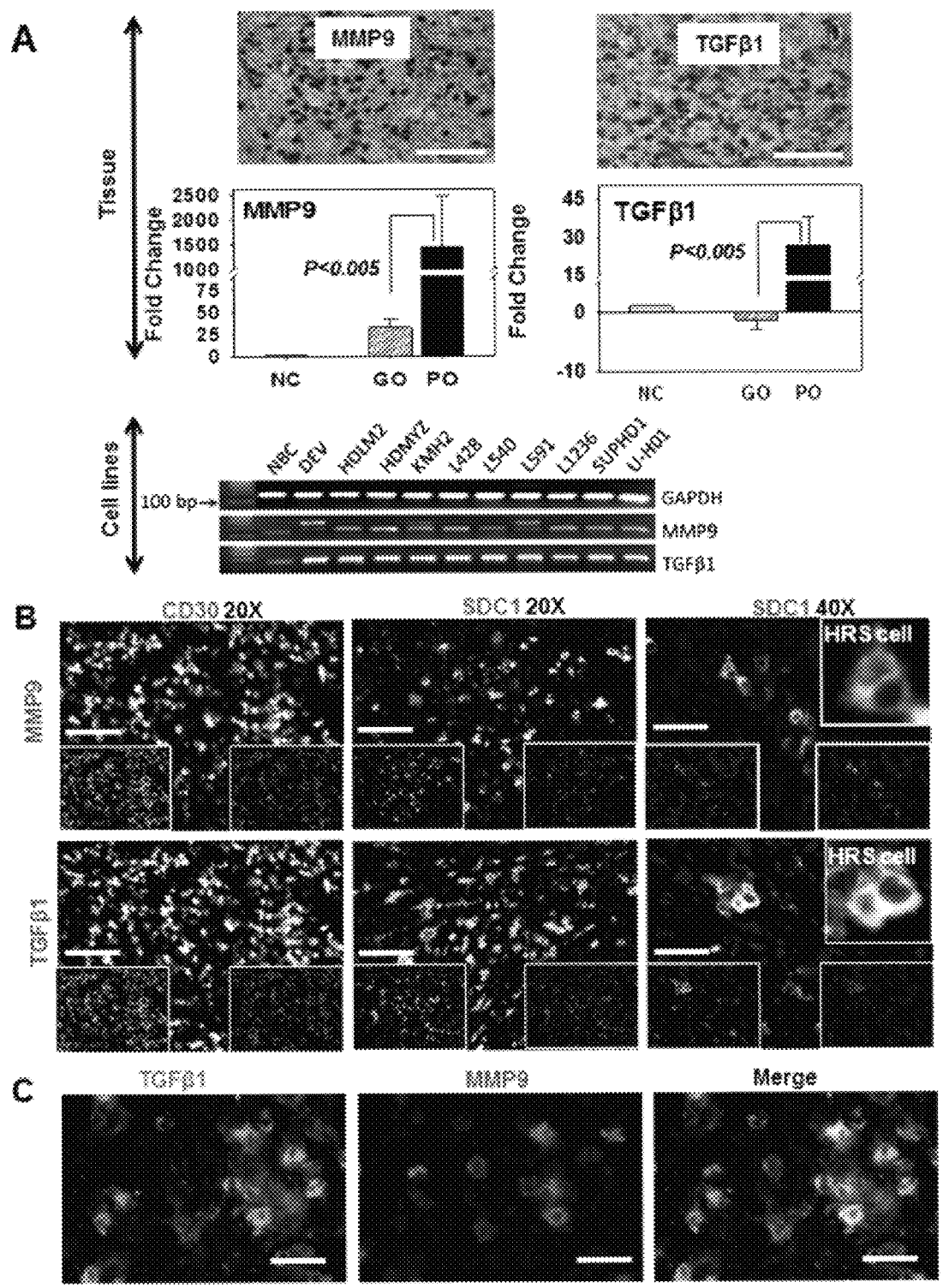
FIG. 4 shows that metastatic markers TGFβ1 and MMP9 are overexpressed in poor outcome HL patients and by HL cell lines. (A) Protein and mRNA expression levels of TGFβ1 and MMP9 in normal lymph node control (NC), good outcome (GO) group and poor outcome (PO) group analyzed by immunostaining (left, images only for PO group) and qRT-PCR (right). mRNA expression is represented by fold-change (y-axis) after normalization with the control (NC). Significance of all qRT-PCR data comparing GO and PO is indicated (p<0.005). TGFβ1 and MMP9 are also overexpressed by the HL cell lines (lower image of gel electrophoresis of (A)). (B) TGFβ1 and MMP9 protein coexpression in tissues from the poor outcome HL patient group analyzed by double immunofluorescence staining for CD30, TGFβ1 and MMP9, or SDC1, TGFβ1 and MMP9. Individual green or red fluorescence is depicted at the bottom of each image. (C) Coexpression of TGFβ1 and MMP9 by subsets of tumor cells in poor outcome sample. (Inset of A and B) Hodgkin Reed Sternberg cells (HRS) coexpressing SDC1 and TGFβ1 or SDC1 and MMP9. Scale bar (white solid bar) represents 100 μm.

The HL tissues from the poor outcome group stained intensely for MMP9 and TGFβ1 compared with the good outcome group and with normal lymph nodes (FIG. 4A). Quantitative analysis by qRT-PCR of MMP9 and TGFβ1 gene expression in the poor outcome group showed increases of 45- and 52-fold, respectively, compared to the good outcome group (after normalization against normal lymph nodes). The mean increase in MMP9 expression in the poor outcome group was 1,457-fold while the good outcome group had levels that were increased by 26-fold compared to normal lymph nodes, suggesting that poor outcome HL tissues have high metastatic potential. Because the HL cell lines potentially represent poor outcome, the expression of MMP9 and TGFβ1 in these cell lines was analyzed by PCR. The results showed that HL cell lines expressed more MMP9 and TGFβ1 than normal B cells (FIG. 4A). Double immunofluorescence analysis showed that a subpopulation of CD30+ cells overexpressed TGFβ1 and MMP9 (FIGS. 4B and 4C), suggesting that CD30+/TGFβ1+ and CD30+/MMP9+ cells may potentiate a metastatic environment that allows CD30+ HL tumor cells to exit the local tumor microenvironment.

The results of this study showed that the established metastatic markers MMP9 and TGFβ1 were overexpressed by subsets of CD30+/FGF2+/SDC1+ cells in tissue samples from PO patients. Classical Hodgkin Lymphoma Reed-Sternberg (HRS) cells are known to produce activated TGFβ1 in primary tumor samples (Newcom S R, Gu L, J Clin Pathol 1995, 48(2): 160-163), while MMP9 overexpression is associated with adverse clinical outcomes in HL (Kuittinen O et al., Eur J Haematol 2002, 69(4): 205-212). Without being bound by theory, these data suggest that HRS cells that harbor the FGF+/SDC1+ immunophenotype and express both MMP9 and TGFβ1 are the cells most likely to be shed from the tumor microenvironment and that the molecular interplay of FGF2, SDC1, MMP9 and TGFβ1 may play a role in HL metastasis.

Example 8

FGF2 and SDC1 are Overexpressed in Putative Circulating CD15+/CD30+ Cells in Poor Outcome (PO) HL Patients To determine whether a subpopulation of CD30+ tumor (i.e., HRS) cells was potentially being shed from the local tumor microenvironment and entering the circulation, we analyzed PBL samples collected from HL patients either prior to first-line treatments (chemo-naive: CN) or after treatment for multiple relapses (chemo-exposed: CE). CD30 and CD15 are markers known to be expressed on classical Hodgkin Lymphoma Reed-Sternberg (HRS) cells.

Figure 5:
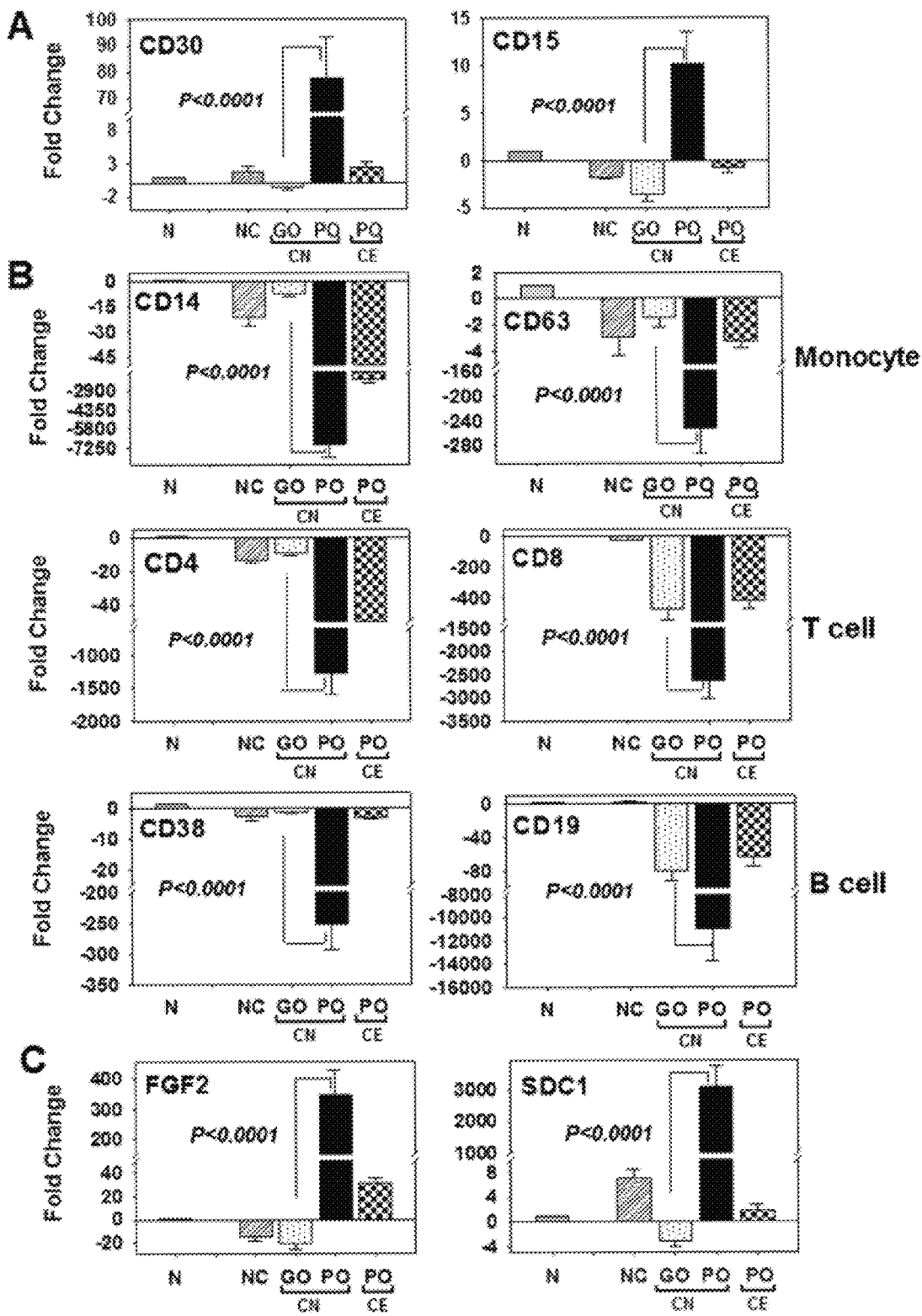
FIG. 5 shows that FGF2 and SDC1 are overexpressed in circulating CD15+/CD30+ cells from chemo-naive poor outcome HL patients. qRT-PCR analysis of cells isolated from the buffy-coat of peripheral blood from normal donor controls (NC, striped bar), chemo-naïve (CN) good outcome (GO, dotted) and CN poor outcome (PO, solid black bar) groups, and chemo-exposed PO group (CE, checkered bar). Expression levels are represented as fold-change (y-axis) after normalization with normal control cells (N, solid gray bar: N denotes B cells in A and C; N denotes monocytes, CD4 T cells, CD8 T cells, and CD19 B cells in B). (A) mRNA expression of CD30 and CD15; (B) cell-specific markers for monocytes (CD14, CD63), T-cells (CD4, CD8), and B-cells (CD38, CD19); (C) FGF2 and SDC1. Significance of all qRT-PCR data comparing chemo-naïve GO and chemo-naïve PO is indicated (p<0.0001; ANOVA and PLSD).

In baseline HL patients, qRT-PCR results showed that cells from the poor outcome group overexpressed CD15 and CD30 by 41-fold and 113-fold, respectively, compared to the good outcome group after normalization with respect to purified B cells (FIG. 5A). In this analysis, the significant increase in marker expression seen for the poor outcome groups was eliminated in the chemo-exposed poor outcome group (FIG. 5A). Without being bound by theory, these data suggest that CD15+/CD30+ cells in the circulation were killed by chemotherapy treatments. A moderate difference in marker expression between the CN good outcome group and the normal control group (n=10) was observed.

To determine if the circulating cells overexpressing CD15+/CD30+ originated from other cell types in the blood, the expression levels of established cell-specific markers, including CD14 (monocytes, macrophages, neutrophils, granulocytes, and dendritic cells), CD63 (basophil activation), CD4 (helper T-cells), CD8 (cytotoxic T cells), CD38 and CD19 (B cells) were analyzed (FIG. 5B). Among CN HL patients, compared to the good outcome group, a significant down-regulation of CD14 (−7,150-fold), CD63 (−966-fold), CD4 (−1,287-fold), CD8 (−2625-fold), CD38 (−253-fold) and CD19 (−10,954-fold) expression was seen for the poor outcome group (FIG. 5B). The expression levels of CD8, CD38, and CD19 in chemo-exposed HL patients were similar to levels in the good outcome group of CN patients, although the down-regulation of CD8 and CD19 expression was significantly lower (−125-fold for CD8 and −19,085-fold for CD19) than that in normal samples. Although the down-regulation of CD14, CD63, CD4, and CD38 among the CN good outcome group of HL patients was similar to normal controls, CD8 and CD19 were significantly down-regulated (CD8 by −125-fold and CD19 by −19,085-fold) in the good outcome CN patients compared to normal samples (FIG. 5B). The down-regulation signatures of the cell markers in the CN poor outcome group were directly opposite that of the CD15+/CD30+ upregulation signature. Without being bound by theory, these data suggest that CD15+/CD30+ cells in the CN poor outcome group were potentially derived from circulating HL tumor cells (FIGS. 5A and 5B). In these circulating cells, FGF2 and SDC1 genes were overexpressed by 17- and 9,764-fold, respectively, compared to the good outcome group (FIG. 5C). This fold-difference was reduced in relapsing HL patients in CE group relative to the CN good outcome group, indicating that FGF2 and SDC1 are robust baseline biomarkers for predicting clinical outcomes for CN HL patients.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A method for treating recurrence of Hodgkin lymphoma (HL) in a subject treated with a first treatment regimen comprising:
   (a) providing a sample from the subject and a sample from each member of a group of two or more classical Hodgkin lymphoma control subjects with chemo-naive relapse free/progression-free/disease free survival of greater than four years;
   (b) isolating total RNA comprising CD30 RNA, Fibroblast Growth Factor-2 (FGF2) RNA, Syndecan-1 (SDC1) RNA, TGFβ1 RNA and MMP9 RNA from the sample from the subject and from the sample from each of the control subjects;
   (c) generating cDNA by reverse transcription of the total RNA from the sample from the subject and the total RNA from the sample from each of the control subjects;
   (d) measuring an amount of CD30 cDNA, FGF2 cDNA, SDC1 cDNA, TGFβ1 cDNA and MMP9 cDNA in the sample from the subject and in the sample from each of the control subjects by quantitative real-time PCR;
   (e) treating the subject with a second treatment regimen, different from the first treatment regimen and effective to treat the recurrence of Hodgkin lymphoma (HL);
   wherein the treating results in clinical improvement of the subject, wherein the amount of the CD30 cDNA, the FGF2 cDNA, the SDC1 cDNA, the TGFβ1 cDNA and the MMP9 cDNA in the Hodgkin Lymphoma (HL) subject is at least 10 fold, 27 fold, 19 fold, 20 fold, and 20 fold higher, respectively, than the mean amount of CD30 cDNA, the FGF2 cDNA, the SDC1 cDNA, the TGFβ1cDNA and the MMP9 cDNA, respectively, in the sample from the control subjects.

2. The method according to claim 1, wherein the sample from the subject and from control subjects is selected from the group consisting of a tumor biopsy, blood, a lymph node and peripheral blood leukocytes (PBL).

3. The method according to claim 1, wherein the amplifying generating cDNA is performed by Reverse Transcriptase-Polymerase Chain Reaction (RT-PCR).

4. A method for detecting cDNA in a poor clinical outcome in a Hodgkin Lymphoma (HL) subject comprising:
   (a) taking a sample from the Hodgkin Lymphoma (HL) subject and a sample from two or more good clinical outcome classical Hodgkin lymphoma control subjects with chemo-naive relapse free/progression-free/disease free survival of greater than four years treated with a first treatment regimen;
   (b) isolating total RNA comprising CD30 RNA, Fibroblast Growth Factor-2 (FGF2) RNA, Syndecan-1 (SDC1) RNA, TGβ1 RNA and MMP9 RNA from the sample from the Hodgkin Lymphoma (HL) subject and from the sample from the good clinical outcome control subjects;
   (c) generating cDNA by reverse transcription of the total RNA from the sample from the subject and the total RNA from the sample from each of the control subjects;
   (d) detecting whether the amount of the CD30 cDNA, the FGF2 cDNA, the SDC1 cDNA, the TGFβ1 cDNA and the MMP9 cDNA in the Hodgkin Lymphoma (HL) subject is at least 10 fold, 27 fold, 19 fold, 20 fold, and 20 fold higher, respectively, than the mean amount of the CD30 cDNA, the FGF2 cDNA, the SDC1 cDNA, the TGβ1 cDNA and the MMP9 cDNA in the good outcome control subjects by measuring an amount of the CD30 cDNA, the FGF2 cDNA, the SDC1 cDNA, the TGβ1 cDNA and the MMP9 cDNA in the Hodgkin Lymphoma (HL) subject and in each of the good clinical outcome control subjects by quantitative real-time PCR.

5. The method according to claim 4, wherein the sample is selected from the group consisting of a tumor biopsy, blood, a lymph node and peripheral blood leukocytes (PBL).

6. The method according to claim 4, wherein the amplifying is performed by Reverse Transcriptase-Polymerase Chain Reaction (RT-PCR).

7. A method of detecting cDNA in a poor clinical outcome Hodgkin Lymphoma (HL) subject treated with a first treatment regimen comprising:
   (a) providing a peripheral blood leukocyte (PBL) sample from the HL subject and a PBL sample from two or more good clinical outcome classical Hodgkin lymphoma control subjects with chemo-naive relapse free/progression-free/disease free survival of greater than four years;
   (b) isolating total RNA comprising CD30 RNA, Fibroblast Growth Factor-2 (FGF2) RNA, Syndecan-1 (SDC1) RNA, TGβ1 RNA and MMP9 RNA from the PBL sample from the HL subject and from the PBL sample from the good clinical outcome control subject;
   (c) generating cDNA by reverse transcription of the total RNA from the sample from the subject and the total RNA from the sample from each of the control subjects;
   (d) detecting whether the amount of the CD30 cDNA, the FGF2 cDNA, the SDC1 cDNA, the TGβ1 cDNA and the MMP9 cDNA in the Hodgkin Lymphoma (HL) subject is at least 10 fold, 27 fold, 19 fold, 20 fold, and 20 fold higher, respectively, than the mean amount of the CD30 cDNA, the FGF2 cDNA, the SDC1 cDNA, the TGFβ1 cDNA and the MMP9 cDNA in the good outcome control subjects by measuring the amount of the CD30 cDNA, the FGF2 cDNA, the SDC1 cDNA, the TGβ1 cDNA and the MMP9 cDNA in the Hodgkin Lymphoma (HL) subject and in each of the good clinical outcome control subjects by quantitative real-time PCR.

8. The method according to claim 7, wherein the generating cDNA is performed by Reverse Transcriptase-Polymerase Chain Reaction (RT-PCR).

9. The method according to claim 7 further comprising:
   (e) measuring the amount of CD15 cDNA in the Hodgkin Lymphoma (HL) subject and in the good clinical outcome control subjects;
   (f) detecting whether the amount of CD15 cDNA in the HL subject is at least 7 fold higher than the mean amount of CD15 cDNA in the good outcome control subjects.

10. The method according to claim 7, wherein the Hodgkin lymphoma subject comprises a metastasis comprising a circulating FGF2+/SDC1+ immunophenotype of a CD30+ cell.

11. The method according to claim 10, wherein the circulating FGF2+/SDC1+ immunophenotype of the CD30+ cell is a Hodgkin Lymphoma and Reed-Sternberg (HRS) cell.

* * * * *

SEQUENCE LISTING

```
<160> NUMBER OF SEQ ID NOS: 36

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
catggcctcc aaggagtaag                                            20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
aggggtctac atggcaactg                                            20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
atgtggcagt gtctgctgag                                            20

<210> SEQ ID NO 4
<211> LENGTH: 20
<212> TYPE: DNA
<213> ORGANISM: Artificial Sequence
```

```
<220> FEATURE:
<223> OTHER INFORMATION: Primer

<400> SEQUENCE: 4
cctagcccaa tgaaaagcag                                              20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
cagagctacc cgcagagttc                                              20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
ctccaaccct gacttgctgt                                              20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
ccaacttagc tgtcccctga                                              20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
ctgggaccaa tgctgttctc                                              20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
gcaggtggga ctttgttgtt                                              20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
ccaaggacaa tccagcactt                                              20
```

```
<210> SEQ ID NO 11
<211> LENGTH: 19
<212> TYPE: DNA
<213> ORGANISM: Artificial Sequence
<220> FEATURE:
<223> OTHER INFORMATION: Primer

<400> SEQUENCE: 11
ttctgcctgt gttcccttg                                                19

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
cacgttcccg tactggttct                                               20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
agatctgagc cagtcgctgt                                               20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
aaaaaggctt ccgtctctgg                                               20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
gagctcagag gttcggaaga                                               20

<210> SEQ ID NO 16
<211> LENGTH: 19
<212> TYPE: DNA
<213> ORGANISM: Artificial Sequence
<220> FEATURE:
<223> OTHER INFORMATION: Primer

<400> SEQUENCE: 16
ttcggagaag ttgcagacg                                                19

<210> SEQ ID NO 17
<211> LENGTH: 20
<212> TYPE: DNA
<213> ORGANISM: Artificial Sequence
<220> FEATURE:
<223> OTHER INFORMATION: Primer
```

<400> SEQUENCE: 17
aaccacactg cttcgatcct                                        20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
aatcccacag cccacagtaa                                        20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
tgctcagcag tcaccatagc                                        20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
cttgaggtgg aagggtctcc                                        20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
cttcacactc cccacacaga                                        20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
ggccactaca gccgtattct                                        20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
cctcaacgac cactttgtca                                        20

<210> SEQ ID NO 24

```
<211> LENGTH: 20
<212> TYPE: DNA
<213> ORGANISM: Artificial Sequence
<220> FEATURE:
<223> OTHER INFORMATION: Primer

<400> SEQUENCE: 24
ccctgttgct gtagccaaat                                               20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
gtacctgaac ccgtgttgct                                               20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
cacgtgctgc tccactttta                                               20

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
ggcgctcatg taccctatgt                                               20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
gccattcacg tcgtccttat                                               20

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
gaagctccac ctgtgctacc                                               20

<210> SEQ ID NO 30
<211> LENGTH: 20
<212> TYPE: DNA
<213> ORGANISM: Artificial Sequence
<220> FEATURE:
<223> OTHER INFORMATION: Primer
```

<400> SEQUENCE: 30
ggtctggaat ccacaagctc                                                    20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
tgacacccac ggttacagag                                                    20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
gtggttttgt ggctcttggt                                                    20

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
taggaccttt ccaccacagc                                                    20

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
gaggctgctt cagtttggag                                                    20

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
tgaggctgag aggtcaaggt                                                    20

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
ctctgttgcc taggctggac                                                    20